United States Patent [19]
Bisset et al.

[11] Patent Number: 5,444,061
[45] Date of Patent: Aug. 22, 1995

[54] ANTI-CANCER COMPOUNDS

[75] Inventors: Graham M. F. Bisset, Sutton; Ann L. Jackman, Wallington; Duncan I. Jodrell, London, all of England

[73] Assignee: British Technology Group Limited, London, England

[21] Appl. No.: 122,473

[22] PCT Filed: Mar. 18, 1992

[86] PCT No.: PCT/GB92/00476

§ 371 Date: Sep. 2, 1993

§ 102(e) Date: Sep. 2, 1993

[87] PCT Pub. No.: WO92/16512

PCT Pub. Date: Oct. 1, 1992

[30] Foreign Application Priority Data

Mar. 19, 1991 [GB] United Kingdom ............. 9105771

[51] Int. Cl.$^6$ ............... A61K 31/505; C07D 239/72
[52] U.S. Cl. .................... 514/259; 514/260; 544/285; 544/287
[58] Field of Search ............ 544/285, 287; 514/259, 514/260

[56] References Cited

U.S. PATENT DOCUMENTS

| | | | |
|---|---|---|---|
| 4,447,608 | 5/1984 | Jones et al. | 544/287 |
| 4,564,616 | 1/1986 | Jones et al. | 514/260 |
| 4,746,659 | 5/1988 | DeGraw et al. | 514/249 |
| 4,767,761 | 8/1988 | Rosowsky | 514/249 |
| 4,981,856 | 1/1991 | Hughes | 514/259 |
| 4,985,441 | 1/1991 | Hughes et al. | 514/260 |
| 4,992,550 | 2/1991 | Hughes | 544/284 |
| 4,996,207 | 2/1991 | Nair et al. | 514/258 |
| 5,081,124 | 1/1992 | Hughes | 514/259 |
| 5,089,499 | 2/1992 | Barker et al. | 514/259 |
| 5,112,837 | 5/1992 | Burrows et al. | 514/312 |
| 5,187,167 | 2/1993 | Hughes | 514/259 |
| 5,236,927 | 8/1993 | Jones et al. | 514/259 |
| 5,252,573 | 10/1993 | Barker et al. | 514/259 |
| 5,280,027 | 1/1994 | Andrew et al. | 514/259 |

FOREIGN PATENT DOCUMENTS 0031237 7/1981 European Pat. Off. .
0204529 11/1987 European Pat. Off. .
2368377 5/1988 European Pat. Off. .

OTHER PUBLICATIONS

Sikora et al "Formation and Retention . . . " Biochem Pharmacol. vol. 37, No. 21 pp. 4147–4164. 1988.
Mueller et al "Inhibition of chicken liver . . . " Biochem Pharmacol. vol. 37 No. 3, pp. 449–451, 1988.
Ng et al "Liposome dependent delivery . . . " Biochimica et Biophysica Acta, 981 (1989) pp. 261–268.
Graham et al "The role of anthrapyrazole . . . " Thirtieth BACR and Fourth ACP Meetings, pp. 501–502. (1989).
Pawelczak et al "Quinazoline antifolates inhibiting . . . " J. Med. Chem. 1989, 32, (1989) pp. 160–165.
Kuefner et al "Occurrence and significance of . . . " Biochemistry 1990, 29, pp. 10540–10545.

(List continued on next page.)

*Primary Examiner*—Cecilia Tsang
*Attorney, Agent, or Firm*—Nixon & Vanderhye

[57] ABSTRACT

Quinazolines of the formula:

[Structural formula showing quinazoline with substituents $R^1$–$R^8$, including HN, O, $R^6$, $R^4$, $R^5$, C–N–Ar–COR$^3$, $R^2$, $R^1$, N, $R^8$, $R^7$]

wherein $R^1$–$R^8$ are defined as in the specification, or a pharmaceutically acceptable salt, ester or amide thereof areof therapeutic value, particularly in the treatment of cancer.

19 Claims, No Drawings

OTHER PUBLICATIONS

Bisset et al "Syntheses and thymidylate synthase . . . " Reprinted from Jour. of Medicinal Chem, 1992, 35, pp. 859–866.

Chemical Abstracts vol. 108, 1988, p. 18. #160929m.

Chemical Abstracts vol. 110, No. 1, p. 27. #50828m. (1989).

T. C. Stephens et al "Use of murine L5178Y" Chem. & Biol. of Pteridines & Folates, New York, 1993, pp. 589–592.

J. Galivan et al. "γ-fluoromethotrexate:Synthesis . . . " Proc Natl Acad Sci. USA, vol. 82, (May 1985), pp. 2598–2602.

J. J. McGuire et al. "Biochemical & Growth . . . " Cancer Research, 49, Aug. 15, 1989, pp. 4517–4525.

J. K. Coward et al. "Fluoroglutamate-containing . . . " Chem. & Biol. of Pteridines, 1989, New York, pp. 1200–1202.

A. H. Calvert et al. "A phase I evaluation . . . " Jour. of Clinical Oncology vol. 4 No. 8 (Aug. 1986), pp. 1245–1252.

B. M. J. Cantwell et al. "Phase II study of a Novel antifolate . . . " Cancer Treatment Reports vol 70 No. 11 Nov. 1986.pp. 1335–1336.

M. F. Bassendine et al. "Induction of remission . . . " Jour of Hepatology, 1987, 4, pp. 349–356.

8th NCI–EORTC Symposium on New Drugs in cancer therapy, p. 40, 132–133. (1994).

B. M. J. Cantwell et al. "Phase II study of the antifolate . . . " Euro. Jour. of Cancer Clin. Oncology, vol. 24 No. 4, 1988, pp. 733–736.

C. Sessa et al. "Phase I study of the antifolate . . . " Euro. Jour. of Cancer Clin. Oncology, vol. 24 No. 4, 1988, pp. 769–775.

ANTI-CANCER COMPOUNDS

This application is a 371 of PCT/GB92/00476 filed Mar. 18, 1992.

This invention relates to novel anti-cancer agents: and more particularly it relates to quinazoline derivatives which possess anti-cancer activity.

One group of anti-cancer agents comprises antimetabolites having anti-folate activity, such as aminopterin and methotrexate. A newer compound of this type which showed considerable promise in clinical trials is known as CB3717 and is described and claimed in United Kingdom Patent Specification No. 2 065 653B. Despite its promising activity against human breast, ovarian and liver cancer, however, CB3717 shows symptoms of toxicity in humans, particularly in relation to the liver and kidneys. Such adverse side effects are reduced in compounds in which the 2-amino substituent of CB3717 is either missing or is replaced by one of various alternative substituents as described and claimed respectively in United Kingdom Patents Nos. 2 175 903 and 2 188 319.

Compounds of this type are believed to act as anti-cancer agents by inhibiting the enzyme thymidylate synthase, which catalyses the methylation of deoxyuridine monophosphate to produce thymidine monophosphate which is required for DNA synthesis. The anti-cancer activity of CB3717 and like compounds may be assessed in vitro by determining their inhibitory effect on that enzyme, and in cell cultures by their inhibitory effect on cancer cell lines such as the mouse leukaemia cell line L1210 and the human breast cancer cell line MCF-7.

Antimetabolites such as aminopterin and methotrexate which are inhibitors of enzymes which utilise folic acid derivatives have also shown promise in the treatment of various allergic diseases such as allergic rhinitis, atopic dermatitis and psoriasis.

We have now found that certain quinazoline derivatives not only show a good level of activity, in particular in respect of their ability to inhibit thymidylate synthase, but also have a different mode of action from CB3717 and other related quinazoline derivatives which have been described. Thus it is believed that CB3717 and more particularly its 2-methyl analogue, which is described and claimed in UK Patent No. 2 188 319, owe anti-tumour activity to an intracellular polyglutamate form but that the compounds of the present invention act directly without being gamma-glutamylated. This alternative mode of action of the compounds of the present invention provides the potential for more precise control in the administration of the compounds to cancer patients, deriving especially from a shorter period of intracellular retention following the completion of administration and a lack of dependence on polyglutamylation which may vary in degree from one patient to another. Moreover, the replacement of the L-glutamic acid residue of CB3717 by an alternative group in the compounds of the present invention will confer different physical properties thereby influencing the overall characteristics of the compounds.

Accordingly the present invention comprises a quinazoline of formula (I):

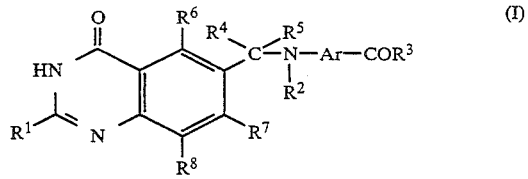

wherein $R^1$ is hydrogen or amino;
or $R^1$ is alkyl, alkoxy or alkylthio each of up to 6 carbon atoms;
or $R^1$ is aryl or aryloxy, each of up to 10 carbon atoms;
or $R^1$ is halogeno, hydroxy or mercapto;
or $R^1$ is alkyl of up to 3 carbon atoms which bears one or more substituents selected from halogeno, hydroxy and alkanoylamino each of up to 6 carbon atoms;
or $R^1$ is alkoxy of up to 3 carbon atoms which bears one or more substituents selected from hydroxy and alkoxy of up to 6 carbon atoms;
wherein $R^2$ is hydrogen or alkyl, alkenyl, alkynyl, hydroxyalkyl, alkoxyalkyl, mercaptoalkyl, alkylthioalkyl, halogenoalkyl, cyanoalkyl, aminoalkyl, alkylaminoalkyl, dialkylaminoalkanol, alkanoylalkyl, carboxyalkyl, carbamoylalkyl or alkanoyl each of up to 6 carbon atoms;
wherein Ar is phenylene or heterocyclene which is unsubstituted or which bears one or more substituents selected from halogeno, cyano, nitro, hydroxy, amino and carbamoyl and alkyl, alkoxy, halogenoalkyl, alkanoylamino and alkoxycarbonyl each of up to 6 carbon atoms;
wherein $R^3$ is the residue of a dipeptide in which the first, N-terminal amino acid residue thereof attached to the carbonyl group of $COR^3$ is an L- or D-amino acid residue —NHCH($CO_2$H)—A—CO— in which A is an alkylene group of up to 6 carbon atoms and the second amino acid residue is of an α-amino acid which has the D-configuration at its asymmetric α-carbon atom;
wherein $R^4$ is hydrogen or alkyl of up to 4 carbon atoms;
wherein $R^5$ is hydrogen or alkyl of up to 4 carbon atoms; and
wherein each of $R^6$, $R^7$ and $R^8$ is hydrogen or alkyl or alkoxy each of up to 4 carbon atoms; or is halogeno; the quinazoline optionally being in the form of a pharmaceutically acceptable salt, ester or amide thereof.

By way of contrast with the corresponding dipeptides of the D,L and particularly the L,L configurations the quinazoline dipeptides of the present invention show a resistance to cleavage of the central amide bond of the dipeptide in vivo.

In this specification the terms alkyl, alkenyl, alkynyl and alkylene include both straight and branched chain groups but references to Individual alkyl or alkylene groups such as "propyl" are specific for the straight chain group only. An analogous convention applies to other generic terms. Moreover, the numbering system for the quinazoline nucleus is the conventional one shown below.

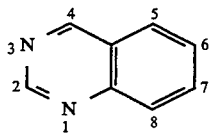

It will be observed that a quinazoline of the invention has at least two asymmetric carbon atoms (present in the peptide residue $R^3$) and can therefore exist in optically active forms. It is to be understood that this invention encompasses the various optically active forms of the quinazoline, subject to the limitation indicated hereinbefore, it being a matter of common general knowledge how such optically active forms may be obtained by stereospecific synthesis or by separation of a mixture of isomeric compounds. One isomer may however be of more interest than another due to the nature of the activity which it exhibits or due to superior physical properties, for example aqueous solubility.

A suitable value for any of $R^1$, $R^2$, $R^4$, $R^5$, $R^6$, $R^7$ or $R^8$ when it is alkyl, or for an alkyl substituent in Ar is, for example, methyl, ethyl, propyl or isopropyl.

A suitable value for $R^2$ when it is alkenyl is, for example, prop-2-enyl, but-2-enyl, but-3-enyl, 2-methylprop-2-enyl, hex-2-enyl, hex-5-enyl or 2,3-dimethylbut-2-enyl.

A suitable value for $R^2$ when it is alkynyl is, for example, prop-2-ynyl, but-2-ynyl, but-3-ynyl, pent-2-ynyl, 3-methylpent-4-ynyl, hex-2-ynyl or hex-5-ynyl.

A suitable value for any of $R^1$, $R^6$, $R^7$ or $R^8$ when it is alkoxy, or for an alkoxy substituent in Ar is, for example, methoxy, ethoxy or isopropoxy.

A suitable value for $R^1$ when it is alkylthio is, for example, methylthio or isopropylthio.

A suitable value for $R^1$ when it is aryl is, for example, phenyl or tolyl.

A suitable value for $R^1$ when it is aryloxy is, for example, phenoxy or tolyloxy.

A suitable value for any of $R^1$, $R^6$, $R^7$ or $R^8$ when it is halogeno is, for example, fluoro, chloro, bromo or iodo.

A suitable value for $R^1$ when it is substituted alkyl is, for example, fluoromethyl, difluoromethyl, trifluoromethyl, 2-fluoroethyl, 3-fluoropropyl, chloromethyl, dichloromethyl, hydroxymethyl, 2-hydroxyethyl, 3-hydroxypropyl, acetamidomethyl, 3-acetamidopropyl or propionamidomethyl.

A suitable value for $R^1$ when it is substituted alkoxy is, for example, 2-hydroxyethoxy, 4-hydroxybutoxy, 3-hydroxy-2-methylpropoxy, 2-methoxyethoxy, 3-methoxypropoxy or 2-ethoxyethoxy.

A suitable value for $R^2$ when it is hydroxyalkyl, alkoxyalkyl, mercaptoalkyl or alkylthioalkyl is, for example 2-hydroxyethyl, 3-hydroxypropyl, 2-methoxyethyl, 2-ethoxyethyl, 3-methoxypropyl, 2-methoxypropyl, 2-mercaptoethyl, 3-mercaptopropyl, 2-methylthioethyl, 3-methylthiopropyl or 2-ethylthioethyl.

A suitable value for $R^2$ when it is halogenoalkyl, cyanoalkyl, aminoalkyl, alkylaminoalkyl or dialkylaminoalkyl is, for example, 2-fluoroethyl, 2-chloroethyl, 2-bromoethyl, 3-fluoropropyl, 3-chloropropyl, cyanomethyl, 2-cyanoethyl, 3-cyanopropyl, 2-aminoethyl, 3-aminopropyl, 3-amino-2-methylpropyl, 2-methylaminoethyl, 2-dimethylaminoethyl, 2-ethylaminoethyl, 2-diethylaminoethyl, 3-methylaminopropyl or 3-dimethylaminopropyl.

A suitable value for $R^2$ when it is alkanoylalkyl, carboxyalkyl, carbamoylalkyl or alkanoyl is, for example, acetonyl, 2-acetylethyl, propionylmethyl, 2-propionylethyl, 3-acetylpropyl, 4-acetylbutyl, carboxymethyl, 2-carboxyethyl, carbamoylmethyl, acetyl, propionyl or butyryl.

A suitable value for Ar when it is phenylene is, for example, 1,3- or particularly 1,4-phenylene.

A suitable value for Ar when it is heterocyclene is, for example, a 5-membered or 6-membered aromatic (that is, fully unsaturated) heterocyclene diradical which contains up to 2 heteroatoms selected from the group consisting of oxygen, nitrogen and sulphur, for example thienylene, pyridylene, pyrimidinylene, thiazolylene or oxazolylene. Of particular interest are compounds in which Ar is pyrimidinylene, particularly pyridylene or especially phenylene.

A suitable halogeno, halogenoalkyl, alkanoylamino or alkoxycarbonyl substituent in Ar is, for example, fluoro, chloro, bromo, iodo, fluoromethyl, difluoromethyl, trifluoromethyl, acetamido, propionamido, isopropionamido, methoxycarbonyl, ethoxycarbonyl or isobutoxycarbonyl.

A suitable level of substitution in At, where substitution is present, is three substituents, particularly two substituents or especially one substituent; and one or two substituents may conveniently be at positions adjacent to the atom bonded to the group $—COR^3$, halogeno substituents such as fluoro being preferred.

The first amino acid residue of the peptide residue $R^3$ may be of the D-configuration at its asymmetric α-carbon atom with the configuration of the peptide then being D,O but this first residue is preferably of the L-configuration, the configuration of the peptide then being L,D.

Although the compounds of the present invention can exist in racemic form, it is preferred that they are optically active. In particular, the L, D- or D,D-quinazoline dipeptide is conveniently substantially free from the L,L-dipeptide and preferably is substantially free from both the L,L- and the D,L-dipeptides. Conveniently it may also be substantially free from the other form D,D or L,D. In its preferred form, therefore, the dipeptide Is substantially free of all of the other three isomeric forms. The term "substantially free" is used herein to indicate the presence of no more than 20% and especially no more than 10% by weight of the other isomer or isomers referred to.

As indicated, the second amino acid residue of $R^3$ is of an α-amino acid in which the α-carbon atom is asymmetric, i.e. the carbon atom in question of the amino acid residue is bonded to four groups which differ from each other, one of which is a carboxy group and another of which contains a grouping

bonded to the carbon atom.

A suitable value for $R^3$ is a dipeptide residue in which the first, N-terminal amino acid residue —NH—CH(CO$_2$H)—A—CO— is linked to the second amino acid residue —NH—CH(Y)—CO$_2$H to provide a group of the formula —NH—CH(CO$_2$H)—A—CONHCH(Y)—CO$_2$H in which A is as defined hereinbefore;

Y is alkyl; alkenyl or alkynyl each of up to 6 carbon atoms;

or Y is alkyl of up to 6 carbon atoms which bears one or more substituents selected from amino, carboxy, hydroxy and mercapto;

or Y is phenyl or benzyl. An alternative value for $R^3$ is a dipeptide residue in which the first, N-terminal amino acid residue —NH—CH($CO_2H$)—A—CO—, A being defined as hereinbefore, is linked to another second amino acid residue than those described above which corresponds to the residue of a naturally occurring amino acid but in the D-configuration.

A suitable value for A is a group of 1, 3 or particularly 2 carbon atoms, for example $CH_2$, $CH_2CH_2CH_2$ and especially $CH_2CH_2$.

A suitable value for Y when it is alkyl is as specified for $R^1$, etc., but particularly butyl and propyl and their branched chain isomers, ethyl, and especially methyl. A suitable value for Y when it is alkenyl or alkynyl is as specified for $R^2$ but particularly prop-2-enyl and prop-2-ynyl. A suitable value for Y when it is a substituted alkyl group is a group which carries one substituent only, particularly a carboxy group, with that substituent conveniently being on a terminal carbon atom of the alkyl group. Such groups are of particular interest among the various possibilities for Y. Of especial interest are alkyl groups of up to 3 carbon atoms, i.e. methyl, ethyl, propyl and isopropyl, although larger groups can be of interest, particularly when branched. Preferred groups Y of this type are thus $CH_2CO_2H$ or $CH_2CH_2CH_2CO_2H$, particularly $CH_2CH(CH_3)CO_2H$ or $CH(CH_3)CH_2CO_2H$ and especially $CH_2CH_2CO_2H$.

Examples of naturally occurring amino acids $H_2NCH(Y)CO_2H$ containing a group Y which may be present in the group $R^3$ of the quinazolines of the present invention (these being either a group Y as specifically discussed above or other forms of group) are alanine (Y=$CH_3$), arginine (Y=$(CH_2)_3NHC(NH_2)$=NH), aspartic acid (Y=$CH_2CO_2H$), cysteine (Y=$CH_2SH$), glutamic acid (Y=$CH_2CH_2CO_2H$), isoleucine (Y=$CH(CH_3)CH_2CH_3$), leucine (Y=$CH_2CH(CH_3)CH_3$), ornithine (Y=$(CH_2)_3NH_2$), phenylalanine (Y=$CH_2C_6H_5$), serine (Y=$CH_2OH$) and valine (Y=$CH(CH_3)_2$). (It will be appreciated that although the group Y is one present in a naturally occurring amino acid, the second amino acid residue is itself of the D-configuration.)

Examples of amino acids $H_2NCH(Y)CO_2H$ which are not naturally occurring which contain groups Y that may be present in the group R of the compounds of the present invention are norvaline (Y=$CH_2CH_2CH_3$), norleucine (Y=$(CH_2)_3CH_3$), 2-phenylglycine (Y=$C_6H_5$) and tert-leucine (Y=$C(CH_3)_3$).

Preferred groups $R^3$ are thus of the formula

—NHCH(COOH)$CH_2CH_2$CONHCH(Y')—$CO_2H$ (1)

and especially

—NHCH(COOH)$CH_2CH_2$CONHCH($CO_2H$)—$(CH_2)_mCO_2H$ (2)

in which Y' is methyl, ethyl, propyl, hydroxymethyl, phenyl or benzyl and m is 1, particularly 3 and especially 2 with the first, glutamic acid residue conveniently being of the L-configuration and with the second amino acid residue being of the D-configuration.

Specific examples of $R^3$ are the residue of the dipeptides γ-glutamyl-aspartic acid, γ-glutamyl-2-aminoadipic acid and particularly γ-glutamyl-alanine, and most especially γ-glutamyl-glutamic acid, in the D,D or preferably the L,D form.

A suitable pharmaceutically-acceptable salt form of a quinazoline of the invention is, for example, an acid addition salt with an inorganic or organic acid, for example hydrochloric, hydrobromic, trifluoroacetic or maleic acid; or an alkali metal, for example sodium, an alkaline earth metal, for example calcium, or ammonium, for example tetra(2-hydroxyethyl)ammonium, salt.

A suitable pharmaceutically-acceptable ester form of a quinazoline of the invention is, for example, an ester with an aliphatic alcohol of up to 6 carbon atoms, for example a methyl, ethyl or tert-butyl ester.

A suitable pharmaceutically-acceptable amide form of a quinazoline of the invention is, for example, an unsubstituted amide of the form —$CONH_2$ or particularly a benzyl substituted amide of the form —$CONHCH_2C_6H_5$.

It is to be understood that $R^3$ may contain several carboxy groups. When it comprises three carboxy groups as is the case for various of the preferred dipeptide residues $R^3$, for example when $R^3$ consists of two glutamic acid residues, a salt or ester may be mono-acid-di-salt or -ester or -amide or it may be a di-acid-mono-salt or -ester or -amide or even a tri-salt or -ester or -amide.

Particularly preferred values for the various symbols $R^1$ to $R^8$ and Ar individually are as expressed for the preferred quinazolines described hereinafter. Moreover, in the case of $R^4$, $R^5$, $R^6$ and $R^8$ compounds in which each of these is hydrogen are of especial interest. With $R^7$, however, compounds in which this is other than hydrogen, for example being one of the groups methoxy, fluoro and chloro and particularly an alkyl group such as methyl, are also of especial interest.

A preferred quinazoline of the invention has the formula stated above wherein $R^1$ is halogeno- or hydroxy-substituted alkyl or particularly hydrogen, amino, alkyl or alkoxy, especially fluoromethyl, hydroxymethyl, hydrogen, amino, methyl, ethyl or methoxy;

wherein $R^2$ is methyl, ethyl, prop-2-enyl, prop-2-ynyl, 2-hydroxyethyl, 3-hydroxypropyl, 2-fluoroethyl or acetonyl;

wherein Ar is 1,4-phenylene, 2-fluoro-1,4-phenylene or 2,6-difluoro-1,4-phenylene;

wherein $R^3$ is the residue of the dipeptide γ-glutamyl-aspartic acid, -glutamic acid, -2-aminoadipic acid or -alanine in either of the L,D and D, D forms;

wherein $R^4$ is hydrogen or methyl;

wherein $R^5$ is hydrogen;

wherein $R^6$ is hydrogen or chloro;

wherein $R^7$ is hydrogen, methyl, fluoro or chloro, and wherein $R^8$ is hydrogen, methoxy or chloro.

An especially preferred quinazoline of the invention has the formula stated above wherein $R^1$ is methyl;

wherein $R^2$ is methyl, ethyl or preferably prop-2-ynyl;

wherein Ar is 1,4-phenylene or 2-fluoro-1,4-phenylene;

wherein $R^3$ is γ-L-glutamyl-D-glutamic acid;

wherein $R^4$ is hydrogen or methyl;

wherein $R^5$ is hydrogen;

wherein $R^6$ is hydrogen or chloro;
wherein $R^7$ is hydrogen, methyl, methoxy, fluoro or chloro and
wherein $R^8$ is hydrogen, methyl, methoxy or chloro.

Other quinazolines of the invention of particular interest have the values of $R^1$, $R^2$, $R^4$ to $R^8$ and Ar in combination as indicated above but with $R^3$ having any value as indicated hereinbefore. However, specific particularly preferred quinazolines of the invention are:

N-p-[N-(3,4-dihydro-2-amino-4-oxoquinazolin-6-ylmethyl)-N-methylamino]benzoyl-L-γ-glutamyl-D-glutamic acid, N-p-[N-(3,4-dihydro-2-amino-4-oxoquinazolin-6-ylmethyl)-N-ethyl amino]benzoyl-L-γ-glutamyl-D-glutamic acid, N-p-[N-(3,4-dihydro-2-amino-4-oxoquinazolin-6-ylmethyl)-N-(prop-2-ynyl)amino]benzoyl-L-γ-glutamyl-D-glutamic acid, N-p-[N-(3,4-dihydro-2-methyl-4-oxoquinazolin-6-ylmethyl)-N-methylamino]benzoyl-L-γ-glutamyl-D-glutamic acid, N-p-[N-(3,4-dihydro-2-methyl-4-oxoquinazolin-6-ylmethyl)-N-ethylamino]benzoyl-L-γ-glutamyl-D-glutamic acid, N-p-[N-(3,4-dihydro-2-methyl-4-oxoquinazolin-6-ylmethyl)-N-(prop-2-ynyl)amino]benzoyl-L-γ-glutamyl-D-glutamic acid, N-p-[N-(3,4-dihydro-2,7-dimethyl-4-oxoquinazolin-6-ylmethyl)-N-methylamino]benzoyl-L-γ-glutamyl-D-glutamic acid, N-p-[N-(3,4-dihydro-2,7-dimethyl-4-oxoquinazolin-6-ylmethyl)-N-ethylamino]benzoyl-L-γ-glutamyl-D-glutamic acid, N-p-[N-(3,4-dihydro-2,7-dimethyl-4-oxoquinazolin-6-ylmethyl)-N-(prop-2-ynyl)amino]benzoyl-L-γ-glutamyl-D-glutamic acid, N-p-[N-(3,4-dihydro-2-methoxy-4-oxoquinazolin-6-ylmethyl)-N-methylamino]benzoyl-L-γ-glutamyl-D-glutamic acid, N-p-[N-(3,4-dihydro-2-methoxy-4-oxoquinazolin-6-ylmethyl)-N-ethylamino]benzoyl-L-γ-glutamyl-D-glutamic acid, N-p-[N-(3,4-dihydro-2-methoxy-4-oxoquinazolin-6-ylmethyl)-N-(prop-2-ynyl)amino]benzoyl-L-γ-glutamyl-D-glutamic acid, N-p-[N-(3,4-dihydro-2-amino-4-oxoquinazolin-6-ylmethyl)-N-methylamino]-o-fluorobenzoyl-L-γ-glutamyl-D-glutamic acid, N-p-[N-(3,4-dihydro-2-amino-4-oxoquinazolin-6-ylmethyl)-N-ethylamino]-o-fluorobenzoyl-L-γ-glutamyl-D-glutamic acid, N-p-[N-(3,4-dihydro-2-amino-4-oxoquinazolin-6-ylmethyl)-N-(prop-2-ynyl)amino]-o-fluorobenzoyl-L-γ-glutamyl-D-glutamic acid, N-p-[N-(3,4-dihydro-2-methyl-4-oxoquinazolin-6-ylmethyl)-N-methylamino]-o-fluorobenzoyl-L-γ-glutamyl-D-glutamic acid, N-p-[N-(3,4-dihydro-2-methyl-4-oxoquinazolin-6-ylmethyl)-N-ethylamino]-o-fluorobenzoyl-L-γ-glutamyl-D-glutamic acid, N-p-[N-(3,4-dihydro-2-methyl-4-oxoquinazolin-6-ylmethyl)-N-(prop-2-ynyl)amino]-o-fluorobenzoyl-L-γ-glutamyl-D-glutamic acid, N-p-[N-(3,4-dihydro-2,7-dimethyl-4-oxoquinazolin-6-ylmethyl)-N-methylamino]-o-fluorobenzoyl-L-γ-glutamyl-D-glutamic acid, N-p-[N-(3,4-dihydro-2,7-dimethyl-4-oxoquinazolin-6-ylmethyl)-N-ethylamino]-o-fluorobenzoyl-L-γ-glutamyl-D-glutamic acid, N-p-[N-(3,4-dihydro-2,7-dimethyl-4-oxoquinazolin-6-ylmethyl)-N-(prop-2-ynyl)amino]-o-fluorobenzoyl-L-γ-glutamyl-D-glutamic acid, N-p-[N-(3,4-dihydro-2-methoxy-4-oxoquinazolin-6-ylmethyl)-N-methylamino]-o-fluorobenzoyl-L-γ-glutamyl-D-glutamic acid, N-p-[N-(3,4-dihydro-2-methoxy-4-oxoquinazolin-6-ylmethyl)-N-ethylamino]-o-fluorobenzoyl-L-γ-glutamyl-D-glutamic acid, and N-p-[N-(3,4-dihydro-2-methoxy-4-oxoquinazolin-6-ylmethyl)-N-(prop-2-ynyl)amino]-o-fluorobenzoyl-L-γ-glutamyl-D-glutamic acid;

as well as pharmaceutically acceptable salts, esters and amides thereof.

In this specification the amino-acid residues are designated in the standard manner (Pure and Applied Chemistry, 1974, 40, 317 and European Journal of Biochemistry, 1984, 138, 9). For the avoidance of doubt, however, it should be noted that γ-glutamyl denotes the radical $H_2NCH(CO_2H)CH_2CH_2CO-$ or $-NHCH(CO_2H)CH_2CH_2CO-$ according to the context.

A quinazoline of the invention may be prepared by any process known to be applicable to the preparation of chemically-related compounds.

The particularly preferred process for the manufacture of a quinazoline of the invention comprises the reaction of an acid of the formula:

[Chemical structure showing a benzene ring with substituents $R^9$, N, $R^1$, N, $R^6$, $R^4$, $R^8$, $R^7$ and a carbonyl group attached to $-C(R^5)-N(R^2)-Ar-CO_2H$]

or a reactive derivative thereof, with the terminal amino group of a dipeptide of the formula $R^3$-H wherein $R^1$, $R^2$, $R^3$, $R^4$, $R^5$, $R^6$, $R^7$, $R^8$ and Ar have the meanings stated above, any mercapto, amino and alkylamino group in $R^1$, $R^2$, $R^3$ and Ar and any carboxy group in $R^1$, $R^2$ and Ar is protected by a conventional protecting group, and any hydroxy group in $R^1$, $R^2$, $R^3$ and Ar and any carboxy group in $R^3$ may be protected by a conventional protecting group or alternatively such a hydroxy or carboxy group need not be protected; $R^9$ is hydrogen or a protecting group whereafter any undesired protecting group including any protecting group $R^9$ is removed by conventional means. The reference to the protection of any amino group in $R^3$ does not of course apply to the terminal amino group of the dipeptide $R^3$—H.

In this process, and the others described hereinafter, the compound $R^3$—H, and also the quinazoline acid where appropriate, conveniently has the stereochemical configuration at the asymmetric carbon atoms therein which is desired in the final quinazoline of formula (I).

A suitable reactive derivative of an acid of the formula given above may be, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate: an active ester, for example an ester formed by the reaction of the acid and a phenol sub as pentafluorophenol or an alcohol such as 1-hydroxybenzotriazole; the product of the reaction of the acid and a carbodiimide, for example dicyclohexylcarbodiimide; or particularly an acyl azide, for example an azide formed by the reaction of the acid and an azide such as diphenylphosphoryl azide or an acyl phosphonate, for example an acyl phosphonate formed by the reaction of the acid and a phosphonate such as diethylcyano phosphonate or (1H-1,2,3-benzotriazol-1-yloxy)-tris(pyrrolidino)-phosphonium hexafluorophosphate.

A suitable protecting group for a hydroxy group is, for example, an esterifying group, for example an acetyl or benzoyl group, which may be removed by hydrolysis with a base, for example sodium hydroxide, or provided that $R^2$ does not contain an alkenyl or alkynyl group, the protecting group may be, for example, an α-arylalkyl group, for example a benzyl group, which may be removed by hydrogenation over a catalyst, for example palladium-on-charcoal.

A suitable protecting group for an amino group may be, for example, an alkoxycarbonyl group, for example a tert-butyloxycarbonyl group which may be removed by treatment with an organic acid, for example trifluoroacetic acid; or it may be, for example, a benzyloxycarbonyl group which may be removed by treatment with a Lewis acid, for example boron tris(trifluoroacetate).

A suitable alternative protecting group for a primary amino group is, for example, a phthaloyl group which may be removed by treatment with an alkylamine, for example dimethylaminopropylamine or with hydrazine.

A suitable protecting group for a carboxy group may be an esterifying group, such as a tert-butyl group which may be removed by treatment with an organic acid, for example trifluoroacetic acid, thereby avoiding the possibility of racemization which can arise with groups removable by base.

A suitable protecting group for a mercapto group is, for example, an esterifying group, for example an acetyl group, which may be removed by hydrolysis with a base, for example sodium hydroxide.

$R^9$ is preferably hydrogen rather than a protecting group but a suitable value for $R^9$ when it is a protecting group is, for example, a pivaloyloxymethyl group. Such a group may be removed by hydrolysis with a base, for example sodium hydroxide, but care should be taken to avoid racemization.

The protecting groups for the various carboxy groups in $R^3$ may be esterifying groups such as permit the product after removal of any undesired protecting group in $R^1$, $R^2$, $R^3$ and Ar and of any protecting group $R^9$ to fall within the definition of a quinazoline of the invention. In such instance the esterified carboxy groups in $R^3$ may if desired be retained in the final product. Alternatively a different protecting group may be used in $R^3$ which will be removed.

The dipeptide of the formula $R^3$—H may be obtained by any of the various general methods of peptide synthesis which are described in the literature of peptide chemistry. Classical methods involving reaction in solution or solid phase methods may both be used. Preferably, however, the dipeptide is prepared by reaction of the appropriate two amino acids in solution, the amino group of the acid providing the N-terminal residue of $R^3$—H and the carboxy group of the acid providing the C-terminal residue of $R^3$—H being protected, for example by protecting groups as described hereinbefore, particularly suitable groups being a benzyloxycarbonyl group and a tert-butyl esterifying group, respectively. Although the amino protecting group will necessarily be removed before reaction of $R^3$—H with the carboxylic acid it may be convenient to retain the carboxy protecting group which is already present.

The carboxylic acid used as starting material may be obtained by the reaction of a compound of the formula:

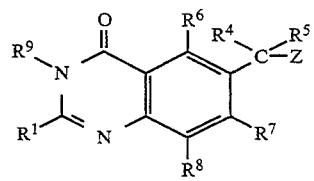

wherein $R^1$, $R^4$, $R^5$, $R^6$, $R^7$, $R^8$ and $R^9$ have the meanings stated above, and Z is a displaceable group, with a compound of the formula:

$HNR^2$—Ar—$CO_2R^{10}$ wherein $R^2$ and Ar have the meanings stated above and $R^{10}$ is a protecting group which can be removed to provide a carboxylic acid.

Z may be, for example, a halogeno or sulphonyloxy group, for example a chloro, bromo, methanesulphonyloxy or toluene-p-sulphonyloxy group.

$R^{10}$ may be, for example, a methyl or an ethyl group which may be removed by hydrolysis with a base, for example sodium hydroxide or $R^{10}$ may be, for example, a tert-butyl group which may be removed by cleavage with an organic acid, for example trifluoroacetic acid.

The protecting group for the carboxy group in $R^{10}$ may be, for example, an esterifying group which can be removed while the protecting group for any mercapto, amino, carboxy and hydroxy group in $R^1$, $R^2$ and Ar is retained.

An alternative procedure for the preparation of the carboxylic acid starting material involves the use of carboxypeptidase G2 enzyme to remove the L-glutamic acid residue from a compound of formula (I) but in which $R^3$ is instead such a residue.

A further preferred process for the manufacture of a quinazoline of the invention, wherein $R^1$ is alkoxy, aryloxy or alkoxy of up to 3 carbon atoms which bears one or more substituents selected from hydroxy and alkoxy of up to 6 carbon atoms, comprises the reaction of a compound of the formula:

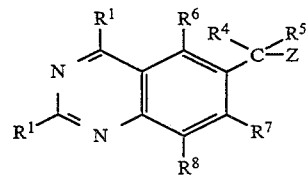

with a compound of the formula:

$HNR^2$—Ar—$COR^3$ wherein $R^1$ has the last-mentioned meaning stated above; wherein $R^2$, $R^3$, $R^4$, $R^5$, $R^6$, $R^7$, $R^8$, Ar and Z have the meanings stated above, provided that any mercapto, amino, alkylamino and carboxy group in $R^2$, $R^3$ and Ar is protected by a conventional protecting group, for example as stated above, and any hydroxy group in $R^1$, $R^2$, $R^3$ and Ar may be protected by a conventional protecting group, for example as stated above, or alternatively any hydroxy group need not be protected; whereafter any undesired protecting group is removed by conventional means, for example as stated above, and the $R^1$ group situated at the 4-position of the quinazoline ring is cleaved by hydrolysis with a base, for example sodium hydroxide, to form a quinazoline of the invention.

A further preferred process for the manufacture of a quinazoline of the invention, wherein $R^1$ is mercapto or alkylthio comprises the reaction of a quinazoline of the formula:

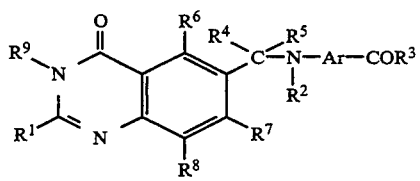

wherein $R^1$ is halogeno or halogenoalkyl and $R^2$, $R^3$, $R^4$, $R^5$, $R^6$, $R^7$, $R^8$, $R^9$ and Ar have the meanings stated above, provided that any mercapto, amino, alkylamino, carboxy and hydroxy group in $R^2$, $R^3$ and Ar may be protected by a conventional protecting group, for example as stated above, or alternatively any amino, alkylamino, carboxy and hydroxy group need not be protected; with thiourea to provide a compound wherein $R^1$ is mercapto; or with an alkyl thiol to provide a compound wherein $R^1$ is alkylthio, arylthio whereafter any undesired protecting group including any protecting group $R^9$ is removed by conventional means, for example as stated above.

A further preferred process for the manufacture of a quinazoline of the invention wherein $R^1$ is alkylthio comprises the reaction of a quinazoline of the formula:

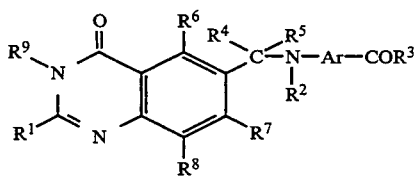

wherein $R^1$ is mercapto and $R^2$, $R^3$, $R^4$, $R^5$, $R^6$, $R^7$, $R^8$, $R^9$ and Ar have the meanings stated above, provided that any mercapto, amino, alkylamino, carboxy and hydroxy group in $R^2$, $R^3$ and Ar may be protected by a conventional protecting group, for example as stated above, or alternatively any amino, alkylamino, carboxy and hydroxy group need not be protected; with a base, for example ammonium hydroxide, followed by alkylation of the resultant thiolate salt with an alkyl halide, for example methyl iodide; whereafter any undesired protecting group including any protecting group $R^9$ is removed by conventional means, for example as stated above.

An alternative process for the manufacture of a quinazoline of the invention comprises the reaction of a compound of the formula:

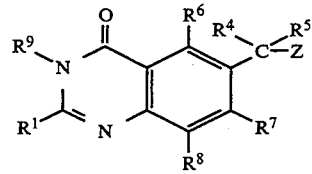

with a compound of the formula:

HNR²—Ar—COR³ and within these compounds $R^1$, $R^2$, $R^3$, $R^4$, $R^5$, $R^6$, $R^7$, $R^8$, $R^9$, and Ar have the meanings stated above, provided that when there is a hydroxy group in $R^1$, $R^3$ or Ar, when there is a hydroxyalkyl group in $R^1$ or $R^2$ when there is a hydroxyalkoxy group in $R^1$, when there is an amino group in $R^1$, $R^3$ or Ar, when there is an aminoalkyl group in $R^2$, when there is an alkylaminoalkyl group in $R^2$, when there is a carboxy or carboxyalkyl group in $R^2$ or $R^3$ or when there is a mercapto or mercaptoalkyl group in $R^1$, $R^2$ or $R^3$ any amino, carboxy and mercapto group is protected by a conventional protecting group, for example as stated above, and any hydroxy group may be protected by a conventional protecting group, for example as stated above, or alternatively any hydroxy group need not be protected; Z is a displaceable group; whereafter any undesired protecting group including any protecting group $R^9$ is removed by conventional means, for example as stated above.

When a novel compound of the formula (I) is required in a pharmaceutically acceptable salt form, it may be obtained, for example, by reaction of said compound with a suitable acid or base using a conventional procedure. When a novel compound of the formula (I) is required in a pharmaceutically acceptable ester form, it may be obtained, for example, by reaction of said compound with a suitable acid or alcohol using a conventional procedure. When a novel compound of the formula (I) is required in a pharmaceutically acceptable amide form, it may be obtained, for example, by reaction of said compound or a suitable derivative thereof such as the acid chloride with ammonia or a suitable amine.

When an optically active form of a compound of the formula (I) is required, it may be obtained by carrying out one of the aforesaid processes using an optically active starting material, or by resolution of a racemic form of said compound using a conventional procedure.

As stated above quinazolines are believed to function as anti-cancer agents at least in part due to their ability to inhibit the enzyme thymidylate synthase. This anti-cancer activity may be assessed, for example, using one or more of the procedures set out below:

(a) An in vitro assay which determines the ability of a test compound to inhibit the enzyme thymidylate synthase. Thymidylate synthase may be obtained in partially purified form from L1210 mouse leukaemia cells and utilised in the assay using the procedures described by Jackman et al (Cancer Res., 1986, 46, 2810);

(b) An assay which determines the ability of a test compound to inhibit the growth of the leukaemia cell line L1210 in cell culture. The test may be similar to that described in UK Patent Specification No. 2065653B; and (c) An assay which determines the ability of a test compound to inhibit the growth of the human breast cancer cell line MCF-7 in cell culture. The test may be similar to that described by Lippman et al (Cancer Res., 1976, 36, 4595).

Although the pharmacological properties of quinazolines of the invention vary with structural change, in general quinazolines of the invention possess thymidylate synthase inhibitory properties at the following concentrations: $IC_{50}$ in the range, for example, 0.001–10 or 20 μM; or quinazolines of the invention possess L1210 cell-line inhibitory properties at the following concentrations: $IC_{50}$ in the range, for example, 0.001–50 or 100 μM.

In general those quinazolines of the invention which are especially preferred possess thymidylate synthase inhibitory properties at the following concentration: $IC_{50}$ of less than 1 μM; or they possess L1210 cell-line inhibitory properties at the following concentration: $IC_{50}$ of less than 10 μM, As regards the inhibition of the MCF-7 cancer cell line, in general quinazolines of the invention possess inhibitory properties at the following concentrations: $IC_{50}$ in the range, for example, 0.1–50 or −100 μM. Especially preferred quinazolines possess MCF-7 cell line inhibitory properties at the following concentration:$IC_{IC50}$ of less than 5 μM.

Thus, by way of example, the quinazoline N-p-[N-(3,4-dihydro-2-methyl-4-oxoquinazolin-6-ylmethyl)-N-(prop-2-ynyl)amino]benzoyl-L-glutamyl-D-glutamic acid, has an $IC_{50}$ of 0.0046 μM against thymidylate synthetase, an $IC_{50}$ of 0.18 μM against the L1210 cell line, an $IC_{50}$ of 0.3 μM against the MCF-7 cell line. In vivo tests in mice at a dosage of 100 mg/kg with various compounds according to the invention have shown a substantial lack of cleavage of the central amide linkage of the dipeptide as assessed by measurement of the amount of the cleavage product as a percentage of the total of parent compound and cleavage product present in the liver or plasma of a mouse sacrificed 1 hour after intraperitoneal administration of the dipeptide, i.e. cleavage was within the limit of experimental detection which is about 5%. Although a minor degree of cleavage of this amide linkage of the quinazoline is acceptable when it is used in practice, a level of cleavage on administration in vivo of less than 10% is preferred, with no more than about 5% being desirable, especially 2% or 1% or less.

A quinazoline of the invention may be administered to a warm-blooded animal, including a human, in the form of a pharmaceutical composition which comprises the quinazoline in association with a pharmaceutically-acceptable diluent or carrier.

The composition may be in a form suitable for oral administration, as a tablet or capsule, or, especially, for parenteral injection or infusion, as a sterile solution, suspension or emulsion, or for topical administration, as an ointment or cream, or for rectal administration as a suppository.

The composition may contain, in addition to the quinazoline of the invention, one or more other anti-cancer substances selected from, for example, mitotic inhibitors, for example vinblastine; alkylating agents, for example cis-platin, carboplatin and cyclophosphamide; other antimetabolites, for example 5-fluorouracil, cytosine arabinoside and hydroxyurea; intercalating antibiotics, for example adriamycin and bleomycin; enzymes, for example asparaginase; topoisomerase inhibitors, for example etoposide and biological response modifiers, for example interferon.

The quinazoline will normally be administered to a warm-blooded animal at a dose within the range 50–25000 mg per square meter body area of the animal, i.e. approximately 1–500 mg/kg. It will be appreciated, however, that where desired dosages outside this range may be employed and, in particular, where the preferred mode of administration involving subcutaneous infusion is used then the dose range may be increased to 1–1000 mg/kg. Preferably a daily dose in the range 1–50 or 1–150 mg/kg is employed, particularly 30–80 mg/kg.

Accordingly the present invention also includes a method for aiding regression and palliation of cancer in a warm-blooded animal such as man, in need of such treatment, which comprises administering to said animal an effective amount of a quinazoline as defined hereinbefore. The invention also provides the use of such a quinazoline in the manufacture of a novel medicament for use in the treatment of cancer.

Quinazolines of the present invention are of interest for a wide range of anti-tumour activities, particularly in the human, including the treatment of breast, ovarian and liver cancer. In addition they are of interest in the context of the treatment of a range of leukaemias, lymphoid malignancies and solid tumours such as carcinomas and sarcomas.

In view of the activity shown by antimetabolites such as aminopterin and methotrexate, which is discussed hereinbefore, the quinazolines of the present invention are also of interest for use in the treament of other conditions, for example allergic conditions such as psoriasis. In using a quinazoline of the invention for such a purpose the compound will normally be administered at a dose within the range 50–25000 mg per square meter body area of the animal, i.e. approximately 1–500 mg/kg. It will be appreciated, however, that where desired dosages outside this range may be employed. In general, for the treatment of an allergic condition such as psoriasis topical administration of a quinazoline of the invention is preferred. Thus, for example, for topical administration a daily dose in the range, for example, of 1–50 or 1–150 mg/kg may be used, particularly 30–80 mg/kg.

Compositions containing the quinazolines may be formulated in unit dosage form, i.e. in the form of discrete portions each comprising a unit dose, or a multiple or sub-multiple of a unit dose, for example an amount of the quinazoline in the range of 1–250 or 500 mg.

The invention is illustrated by the following Examples.

The structures of all compounds of the invention were confirmed by proton magnetic resonance and mass spectroscopy and by elemental analysis. Proton magnetic resonance and mass spectra were determined using a Bruker WM250 spectrometer operating at a field strength of 250 MHz. Chemical shifts are reported in parts per million downfield from tetramethylsilane as an internal standard (δ scale) and peak multiplicities are shown thus: s, singlet; d, doublet; d of d's, doublet of doublets; t, triplet; m, multiplet, the attribution believed to be appropriate for each signal also being indicated. Mass spectra were obtained using a VG analytical ZAB SE spectrometer with fast-atom bombardment ionization (FAB) or a Finnigan TSQ 700 spectrometer with electrospray ionization (ESI). Where appropriate, either positive ion data or negative ion data were collected. Column chromatography was performed using Merck Art 15111 silica gel.

Intermediates for the preparation of compounds according to the invention containing other groups $R^1$, $R^2$, $R^4$ to $R^8$ and Ar are described in UK patents 2 065 653, 2 175 903, 2 188 319 and 2 202 847 and in UK patent applications 2 217 709, 2 227 016 and 2 244 708, and in the equivalents thereof filed in other countries.

EXAMPLES

Example 1

N-p-[N-(3,4-Dihydro-2-methyl-4-oxoquinazolin-6-ylmethyl)-N-(prop-2-ynyl)amino]benzoyl-L-γ-glutamyl-D-glutamic acid (1) Tri-tert-butyl-L-γ-glutamyl-D-glutamate D-Glutamic acid (5.88 g), tert-butyl acetate (100 ml) and 70% aqueous perchloric acid (6.3 g) were stirred at laboratory temperature for 4 days. The mixture was then cooled in an ice-water bath and extracted with 0.5 N hydrochloric acid (3×100 ml). The combined aqueous extracts were immediately neutralised with solid sodium bicarbonate. The aqueous solution was extracted with diethyl ether (3×100 ml), the ether extracts pooled, dried over anhydrous sodium sulphate and the ether evaporated in vacuo to give di-tert-butyl-D-glutamate (0.855 g).

To a stirred solution of α-tert-butyl-N-benzyloxycarbonyl-L-glutamate (Org. Prep. Proc. Int., 1985, 17, 416; 1.011 g) and N-methylmorpholine (0.303 g) in dry tetrahydrofuran (10 ml) cooled to −20° C. was added isobutyl chloroformate (0.408 g). After 10 minutes a solution of di-tert-butyl-D-glutamate (0.855 g) in tetrahydrofuran (10 ml) was added. Stirring was continued for 10 minutes at −20° C., and then at laboratory temperature for 1 hour. N-methylmorpholine hydrochloride was filtered off and the filtrate evaporated to dryness in vacuo. The residue was dissolved in ethyl acetate (100 ml) and washed with 10% aqueous citric acid (2×50 ml), saturated aqueous sodium bicarbonate (100 ml) and dilute aqueous sodium chloride (100 ml), then dried over anhydrous sodium sulphate, filtered and evaporated in vacuo. The residue was purified by chromatography on a silica gel column using 2% MeOH in dichloromethane as eluant. The product was triturated in hexane and the white solid isolated by filtration, washed with hexane and dried in vacuo. There was thus obtained tri-tert-butyl-N-[N-(benzyloxycarbonyl)-L-γ-glutamyl]-D-glutamate (1.363 g), m.p. 110° C.

NMR Spectrum (CD$_3$SOCD$_3$): 1.39 (s, 27H, C(CH$_3$)$_3$), 1.73, 1.89 (2×m, 4H, β-CH$_2$), 2.23 (m, 4H, γ-CH$_2$), 3.89 (m, 1H, glu$_L$ α-CH), 4.10 (m, 1H, glu$_D$ α-CH), 5.03, 5.04 (ABq J$_{AB}$=14.0 Hz, 2H, ArCH$_2$), 7.36 (m, 5H, ArH), 7.63 (d, J=7.7 Hz, 1H, glu$_L$ NH), 8.13 (d, J=7.7 Hz, 1H, glu$_D$ NH). Mass Spectrum (positive ion FAB): m/e 579 (M+H)$^+$. Elemental Analysis: Found C, 62.30; H, 7.95; N, 4.85%. C$_{30}$H$_{46}$N$_2$O$_9$ requires C, 62.27; H, 8.01; N, 4.84%.

A solution of tri-tert-butyl N-[N-(benzyloxycarbonyl)-L-γ-glutamyl]-D-glutamate (0.867 g) in ethyl acetate containing 10% Pd/C (0.1 g) was stirred under hydrogen for 2.5 hours. The catalyst was removed by filtration and the filtrate evaporated to dryness in vacuo, yielding tri-tert-butyl-L-γ-glutamyl-D-glutamate (0.666 g).

(2) p-[N-(3,4-Dihydro-2-methyl-4-oxoquinazolin-6-ylmethyl)-N-(prop-2-ynyl)amino]benzoic acid A mixture of tert-butyl p-aminobenzoate (Synth. Commun., 1984, 14, 921; 10.5 g), propargyl bromide (7.3 ml of an 80% solution in toluene), potassium carbonate (7.5 g) and N,N-dimethylacetamide (85 ml) was heated to 50° C. for 24 hours, cooled, filtered and evaporated. The residue was purified by chromatography on a silica gel column using a 6:1 v/v mixture of hexane and ethyl acetate as eluant.

A mixture of the product (7.3 g); 6-bromomethyl-3,4-dihydro-2-methylquinazolin-4-one (8 g; prepared as described in Example 3 of UK Patent 2 188 319B), calcium carbonate (3.2 g) and dimethylformamide (100 ml) was stirred at laboratory temperature for 65 hours, filtered and evaporated. The residue was purified by chromatography on a silica gel column using ethyl acetate as eluant.

The mixture of the product (2.5 g) and trifluoroacetic acid (25 ml) was stirred at laboratory temperature for 10 minutes and evaporated to give the p-aminobenzoic acid as its trifluoroacetic acid salt (2.5 g).

(3) N-p-[N-(3,4-dihydro-2-methyl-4-oxoquinazolin-6-ylmethyl)-N-(prop-2-ynyl)amino]benzoyl-L-γ-glutamyl-D-glutamic acid A mixture of p-[N-(3,4-dihydro-2-methyl-4-oxoquinazolin-6-ylmethyl)-N-(prop-2-ynyl)amino]benzoic acid, trifluoroacetate salt (0.461 g) and tri-tert-butyl-L-γ-glutamyl-D-glutamate (0.666 g) was dissolved in dry dimethylformamide (15 ml) at laboratory temperature and to this solution was added diethyl cyanophosphonate (0.359 g) and then triethylamine (0.222 g). The mixture was stirred under nitrogen and in the dark for 2.5 hours and then diluted with ethyl acetate (100 ml) and water (100 ml). The water layer was separated and extracted with ethyl acetate (2×100 ml). The combined ethyl acetate extracts were washed with 10% aqueous citric acid (2×50 ml), saturated aqueous sodium bicarbonate (100 ml) and dilute aqueous sodium chloride (100 ml), then dried over anhydrous sodium sulphate, filtered and evaporated in vacuo.

The residue was purified by chromatography on a silica gel column using 1% methanol in ethyl acetate as eluant. The product was crystallised from dichloromethane/hexane and there was thus obtained tri-tert-butyl-N-p-[N-(3,4-dihydro-2-methyl-4-oxoquinazolin-6-ylmethyl)-N-(prop-2-ynyl)amino]benzoyl-L-γ-glutamyl-D-glutamate (containing 0.5 equivalents of water; 0.467 g), m.p. 116°-117° C.

NMR Spectrum (CD$_3$SOCD$_3$): 1.38, 1.40 (2×s, 27H, (CH$_3$)$_3$), 1.72, 1.88, 1.99 (3×m, 4H, β-CH$_2$), 2.24 (t, J=7.4 Hz, 4H, γ-CH$_2$), 2.33 (s, 3H, quinazoline 2-CH$_3$), 3.22 (s, 1H, C≡CH), 4.10 (m, 1H, glu$_D$ α-CH), 4.25 (m, 1H, glu$_L$ α-CH), 4.34 (s, 2H, CH$_2$C≡C), 4.18 (s, 2H, quinazoline 6-CH$_2$), 6.84 (d, J=8.8 Hz, 2H, 3',5'-ArH), 7.54 (d, J=8.4 Hz, 1H, quinazoline 8-14), 7.70 (dd, J=1.6 14z, 1H, quinazoline 7-H), 1.74 (d, J=8.8 Hz, 2',6'-ArH), 7.96 (s, 1H, quinazoline 5-H), 8.15 (d, J=7.5 Hz, 1H, glu$_D$ NH), 8.31 (d, J=7.2 Hz, 1H, glu$_L$ NH), 12.18 (s, 1H, lactam NH). Mass Spectrum (positive ion FAB): m/e 773 (M$^+$); Elemental Analysis: Found C, 64.51; H, 7.12; N, 8.97%. C$_{42}$H$_{55}$N$_5$O$_9$.0.5 H$_2$O requires C, 64.43; H, 7.21; N, 8.95%.

A mixture of tri-tert-butyl-N-p-[N-(3,4-dihydro-2-methyl-4oxoquinazolin-6-ylmethyl)-N-(prop-2-ynyl)amino]benzoyl-L-γ-glutamyl-D-glutamate (0.235 g) and trifluoroacetic acid (10 ml) was stirred at laboratory temperature for 1 hour in the dark and under a nitrogen atmosphere. The solution was then evaporated in vacuo and the residue triturated with diethyl ether (30 ml). The white solid was isolated by filtration, washed with diethyl ether (4×10 ml) and dried in vacuo. There was thus obtained N-p-[N-(3,4-dihydro-2-methyl-4-oxoquinazolin-6-ylmethyl)-N-(prop-2-ynyl)amino]benzoyl-L-γ-glutamyl-D-glutamic acid (containing 1.4 equivalents of trifluoroacetic acid; 0,231 g), m.p. 146°–148° C.

NMR Spectrum: (CD$_3$SOCD$_3$), 1.74, 1.92, 2.04 (3×m, 4H, β-CH$_2$), 2.26 (t, J=7.3 Hz, 4H, γ-CH$_2$), 2.39 (s, 3H, quinazoline 2-CH$_3$), 3.23 (s, 1H, C≡CH), 4.18 (m, 1H, glu$_D$ α-CH), 4.31 (m, 1H, glu$_L$ α-CH), 4.35 (s, 2H, CH$_2$C≡C), 4.80 (s, 2H, quinazoline 6-CH$_2$), 6.84 (d, J=8.8 Hz, 2H, 3′,5′-ArH) 7.57 (d, J=8.4 Hz 1H, quinazoline 8-H), 7.75 (d, J=8.7 Hz. 3H, 2′,6′-ArH, quinazoline 7-H), 7.99 (s, 1H, quinazoline 5-H), 8.15 (d, J=7.7 Hz, 1H, glu$_D$ NH), 8.31 (d, J=7.5 Hz, 1H, glu$_L$ NH), 12.48 (bd, CO$_2$H). Mass Spectrum (positive ion FAB): m/e 606 (M+H)$^+$. Elemental Analysis: Found C, 51.49; H, 4.46; N, 9.49%. C$_{30}$H$_{31}$N$_5$O$_9$.1.4CF$_3$CO$_2$H requires C, 51.48; 11, 4.27; N, 9.15%.

Example 2

N-p-[N-(3,4-dihydro-2-methyl-4-oxoquinazolin-6-ylmethyl)-N-(prop-2-ynyl)amino]benzoyl-L-γ-glutamyl-D-alanine (1) Di-tert-butyl-L-γ-glutamyl-D-alanine To a stirred solution of α-tert-butyl-N-carbobenzoxy-L-glutamate (2.022 g) and N-methylmorpholine (0.606 g) in dry tetrahydrofuran (10 ml) cooled to −20° C. was added isobutyl chloroformate (0.816 g). After 10 minutes a slurry of D-alanine α-tert-butyl ester hydrochloride (1.09 g) and N-methylmorpholine (0.606 g) in tetrahydrofuran (10 ml) was added. Stirring was continued for 10 minutes at −20° C., and then at laboratory temperature for 1 hour. N-methylmorpholine hydrochloride was filtered off and the filtrate evaporated to dryness in vacuo. The residue was dissolved in ethyl acetate (100 ml) and washed with 10% aqueous citric acid (2×50 ml), saturated aqueous sodium bicarbonate (100ml) and dilute aqueous sodium chloride (100 ml), then dried over anhydrous sodium sulphate, filtered and evaporated in vacuo. The residue was purified by chromatography on a silica gel column using dichloromethane:ethyl acetate (2:1 ratio) as eluant. There was thus obtained di-tert-butyl N-[N-(benzyloxycarbonyl)-L-γ-glutamyl]-D-alanine (2.3 g), m.p. 78°–80° C.

NMR Spectrum (CD$_3$SOCD$_3$): 1.21 (d, J=7.3 Hz, 3H, ala-CH$_3$), 1.38, 1.39 (2×s, 18H, C(CH$_3$)$_3$), 1.74, 1.90 (2×m, 2H, β-CH$_2$), 2.18 (t, J=7.5 Hz, 2H, γ-CH$_2$), 3.88 (m, 1H, glu α-CH), 4.06 (m, 1H, ala α-CH), 5.02, 5.03 (ABq, J$_{AB}$=12.5 Hz, 2H, ArCH$_2$), 7.35 (m, 5H, ArH), 7.64 (d, J=7.7 Hz, 1H, glu NH), 8.17 (d, J=7.0 Hz, 1H, ala NH). Mass Spectrum (positive ion FAB): m/e 465 (M+H)$^+$. Elemental Analysis: Found C, 61.74; H, 7.73; N, 6.11%. C$_{17}$H$_{23}$NO$_6$ requires C, 62.05; H, 7.81, N, 6.03%.

A solution of the product (0.696 g) in ethyl acetate containing 10% Pd/C (0.1 g) was stirred under hydrogen for 2.5 hours. The catalyst was removed by filtration and the filtrate evaporated to dryness in vacuo, yielding di-tert-butyl-L-γ-glutamyl-0-alanine (0. 480 g).

(2) N-p-[N-(3,4-dihydro-2-methyl-4-oxoquinazolin-6-ylmethyl)-N-(prop-2-ynyl)amino]benzoyl-L-γ-glutamyl-D-alanine The process described in Example 1(3) was repeated using di-tert-butyl-L-γ-glutamyl-D-alanine (0.48 g) as starting material in place of tri-tert-butyl-L-γ-glutamyl-D-glutamate. There was thus obtained di-tert-butyl-N-p-[N-(3,4-dihydro-2-methyl-4-oxoquinazolin-6-ylmethyl)-N-(prop-2-ynyl)amino]benzoyl-L-γ-glutamyl-D-alanine (0.291 g), m.p. 166°–168° C.

NMR Spectrum (CD$_3$SOCD$_3$): 1.19 (d, J=7.3 Hz, 3H, ala-CH$_3$), 1.37, 1.40 (2×s, 18H, C(CH$_3$)$_3$), 1.96 (m, 2H, β-CH$_2$), 2.23 (m, γ-CH$_2$), 2.32 (s, 3H, quinazoline 2-CH$_3$), 3.23 (s, 1H, C≡CH), 4.07 (quintet, J=7.3 Hz, 1H, ala α-CH), 4.24 (m, 1H, glu α-CH), 4.34 (s, 2H, CH$_2$C≡C), 4.78 (s, 2H, quinazoline 6-CH$_2$), 6.83 (d, J=8.8 Hz, 2H, 3′,5′-ArH) 7.54 (d, J=8.4 Hz, 1H, quinazoline 8-H), 7.69 (dd, 1H, quinazoline 7-H), 7.73 (d, J=8.9 Hz, 2H, 2′,6′-ArH) 7.96 (s, 1H, quinazoline 5-H) 8.19 (d, J=7.0 Hz, 1H, ala NH), 8.31 (d, J=7.2 Hz, 1H, glu NH), 12.19 (s, 1H, lactam NH). Mass Spectrum (positive ion FAB): m/e 660 (M+H)$^+$; Elemental Analysis: Found C, 65.45; H, 7.01; N, 10.43%. C$_{36}$H$_{45}$N$_5$O$_7$ requires C, 65.54; H, 6.87; N, 10.61%.

Di-tert-butyl-N-p-[N-(3,4-dihydro-2-methyl-4-oxoquinazolin-6-ylmethyl)-N-(prop-2-ynyl)amino]benzoyl-L-γ-glutamyl-D-alanine (0.1 g) Has treated with trifluoroacetic acid as described in Example 1(3). There was thus obtained N-p-[N-(3,4-dihydro-2-methyl-4-oxoquinazolin-6-ylmethyl)-N-(prop-2-ynyl)amino]benzoyl-L-γ-glutamyl-D-alanine (containing equivalent of CF$_3$CO$_2$H and 0.7 equivalents of ether; 0.084 g), m.p. 180° C. (decomp).

NMR Spectrum: (CD$_3$SOCD$_3$): 1.21 (d, J=7.3 Hz, 3H, ala-CH$_3$), 1.94, 2.03 (2×m, 2H, β-CH$_2$), 2.22 (m, 2H, γ-CH$_2$), 2.38 (s, 3H, quinazoline 2-CH$_3$), 3.23 (s, 1H, C≡CH), 4.16 (m, 1H, ala α-CH), 4.30 (m, 1H, glu α-CH), 4.34 (s, 2H, CH$_2$C≡C), 4.80 (s, 2H, quinazoline 6-CH$_2$), 6.83 (d, J=8.3 Hz, 2H, 3′,5′-ArH), 7.57 (d, J=8.4 Hz, 1H, quinazoline 8-H), 7.74 (d, J=8,4 Hz, 3H, 2′,6′-ArH, quinazoline 7H), 7.99 (s, 1H, quinazoline 5-H), 8.17 (d, J=7.3 Hz, 1H, ala NH), 8.30 (d, J=7.1 Hz, 1H, glu NH). Mass Spectrum (positive ion FAB): m/e 548 (M+H)$^+$. Elemental Analysis: Found C, 55.09; H, 5.43; N, 9.79%. C$_{28}$H$_{29}$N$_5$O$_7$.CF$_3$CO$_2$H.0.7(C$_2$H$_5$)$_2$O requires C, 55.22; 14, 5.19; N, 9.82%.

Example 3

N-p-[N-(2-Amino-3,4-dihydro-4-oxoquinazolin-6-ylmethyl)-N-(prop-2-ynyl)amino]benzoyl-L-γ-glutamyl-D-glutamic acid.

(1) p-[N-(2-Amino-3,4-dihydro-4-oxoquinazolin-6-ylmethyl)-N-(prop-2-ynyl)amino]benzoic acid, trifluoroacetate salt.

A stock solution of Tris-buffer was prepared by dissolving Trizma base (12.11 g) and zinc chloride (0.035 g) in distilled water (1 liter). N-p-[N-(2-Amino-3,4-dihydro-4-oxoquinazolin-6-ylmethyl)-N-(prop-2-ynyl)amino]benzoyl-L-glutamic acid, disodium salt (1 g) (prepared as described in Example 4 of UK Patent 20656538) was dissolved in Tris buffer (100 ml) at pH 10.4 and the solution adjusted to pit 7.3 using 2N hydrochloric acid, The solution was shaken at 37° C. and the reaction initiated by the addition of carboxypeptidase G2 (200 μL of a stock solution: 1000 units/ml; Eur. J. Biochem., 1985, 148, 447). After 12 hours, the mixture was cooled in ice and adjusted to pH 4 with 2N hydrochloric acid. The precipitate was filtered off, washed with water (2×50 ml) and dried in vacuo over phosphorous pentoxide. There was thus obtained p-[N-(2-amino-3,4-dihydro-4-oxoquinazolin-6-ylmethyl)-N-(prop-2-ynyl)amino]benzoic acid (0.579 g), m.p.>300° C. (decomp.).

NMR Spectrum (CD$_3$SOCD$_3$): 3.24 (d, J=2.0 Hz, 1H, C≡CH), 4.30 (s, 2H, CH$_2$C≡C), 4.68 (s, 2H, quinazoline 6-CH$_2$), 6.40 (s, 2H, quinazoline 2-NH$_2$), 6.84 (d, J=7.3 14z, 2H, 3′,5′-ArH), 7.17 (dd, J=8.3, 1.5 Hz, 1H, quinazoline 7-H) 7.49 (d, J=8.5 Hz, 1H, quinazoline 8-H), 7.76 (d, J=8.2 Hz, 3H, 2′,6′-ArH, quinazoline 5-H), 11.30 (s, 1H, lactam NH).

A mixture of the product (0.579 g) and trifluoroacetic acid (10 ml) was stirred at laboratory temperature for 1 hour in the dark and under a nitrogen atmosphere. The solution was then evaporated in vacuo and the residue triturated with diethyl ether (50 ml). The buff solid was isolated by filtration, washed diethyl ether (4×10 ml) and dried in vacuo. There was thus obtained p-[N-(2-amino-3,4-dihydro-4-oxoquinazolin-6-ylmethyl)-N-(prop-2-ynyl)amino]benzoic acid, trifluoroacetate salt (0.765 g), m.p. 251° C.

NMR Spectrum (CD$_3$SOCD$_3$): 3.27 (s, 1H, C≡CH), 3.70 (s, 1H, CO$_2$H), 4.35 (s, 2H, CH$_2$C≡C), 4.76 (s, 2H, quinazoline 6-CH$_2$), 6.82 (d, J=8.7 Hz, 2H, 3′,5′-ArH) 7.38 (d, J=8.4 Hz 1H, quinazoline 8-H), 7.70 (m, 1H, quinazoline 7-H), 7.75 (d, J=8.7 Hz, 2H, 2′,6′-ArH), 7.88 (s, 1H, quinazoline 5-H), 8.04 (s, 2H, quinazoline 2-NH$_2$), 12.28 (s, 1H, lactam NH).

(2) N-p-[N-(2-Amino-3,4-dihydro-4-oxoquinazolin-6-ylmethyl)-N-(prop-2-ynyl)amino]benzoyl-L-γ-glutamyl-D-glutamic acid.

The process described in Example 1(3) was repeated using p-[N-(2-amino-3,4-dihydro-4-oxoquinazolin-6-ylmethyl)-N-(prop-2-ynyl)amino]benzoic acid, trifluoroacetate salt (0.46 g) as starting material in place of N-p-[N-(3,4-dihydro-2-methyl-4-oxoquinazolin-6-ylmethyl)-N-(prop-2-ynyl)amino]benzoic acid, trifluoroacetate salt. There was thus obtained tri-tert-butyl-N-p-N-(2-amino-3,4-dihydro-4-oxoquinazolin-6-ylmethyl)-N-(prop-2-ynyl)amino]benzoyl-L-γ-glutamyl-D-glutamate (0.532 g), m.p. 12320 -125° C.

NMR Spectrum (CD$_3$SOCD$_3$): 1.38, 1.40 (2×s, 27H, C(CH$_3$)$_3$), 1.71, 1.89, 1,97 (3×m, 4H, β-CH$_2$), 2.24 (m, 4H, γ-CH$_2$), 3.22 (s, 1H, C≡CH), 4.10 (m, 1H, glu$_D$ α-CH), 4.24 (m, 1H, glu$_L$ 4.28 (s, 2H, CH$_2$C≡C), 4.66 (s, 2H, quinazoline 6-CH$_2$), 6.31 (s, 2H, quinazoline 2-NH$_2$), 6.84 (d, J=8.8 Hz, 2H, 3′,5′-ArH) 7.16 (d, J=8.5 Hz 1H, quinazoline 8-H) 7.49 (dd, J=8.3, 1.0 Hz, 1H, quinazoline 7-H), 7.74 (d, J=8.8 Hz, 2H, 2′,6′-ArH) 7.78 (d, J=1.4 Hz, 1H, quinazoline 5-H), 8.16 (d, J=7.6 Hz, 1H, glu$_D$ NH), 8.32 (d, J=7.3 Hz, 1H, gluL NH), 10.94 (s, 1H, lactam NH). Mass Spectrum (positive ion FAB): m/e 775 (M+H)+. Elemental Analysis: Found C, 62.84; H, 7.09; N, 10.74% C$_{41}$H$_{54}$N$_6$O$_9$.0.5H$_2$O Requires C, 62.81; H, 7.07; N, 10.72%.

Tri-tert-butyl-N-p-[N-(2-amino-3,4-dihydro-4-oxoquinazolin-6-ylmethyl)-N-(prop-2-ynyl)amino]benzoyl-L-γ-glutamyl-D-glutamate (0.1 g), was treated with trifluoroacetic acid as described in Example 1(3). There was thus obtained N-p-[N-(2-amino-3,4-dihydro-4-oxoquinazolin-6-ylmethyl)-N-(prop-2-ynyl)amino]benzoyl-L-γ-glutamyl-D-glutamic acid (containing 0.7 equivalents of CF$_3$COOH and 1 equivalent of H$_2$O; 0.099 g), m.p. 211°–213° C.

NMR Spectrum (CD$_3$SOCD$_3$): 1.74, 1.93, 2.04 (3×m, 4H, β-CH$_2$), 2.25 (m, 4H, γ-CH$_2$), 3.23 (s, 1H, C≡CH), 4.18 (m, 1H, glu$_D$ α-CH), 4.32 (m, 3H, CH$_2$C≡C and glu$_L$ α-CH), 4.73 (s, 2H, quinazoline 6-CH$_2$), 6.83 (d, J=8.4 Hz, 2H, 3′,5′-ArH), 7.33 (d, J=8.3 Hz, 1H, quinazoline 8-H), 7.65 (d, J=8.6Hz, 1H, quinazoline 7-H), 7.75 (d, J=8.2 Hz, 4H, 2′,6′-ArH and quinazoline 2-NH$_2$), 7.87 (s, 1H, quinazoline 5-H), 8.16 (d, J=7.5 Hz, 1H, glu$_D$ NH), 8.32 (d, J=7.3 Hz, 1H, glu$_L$ NH), 12.44 (br, CO$_2$H). Mass Spectrum (positive Ion FAB): m/e 629 (M+Na)+. Elemental Analysis: Found C, 51.71; H, 4.54; N, 11.81; F, 5.65% C$_{29}$H$_{30}$N$_6$O$_9$.0.7 CF$_3$COOH.H$_2$O requires C, 51.83; H, 4.68; N, 11.93; F, 5.66%.

Example 4

N-p-[N-(3,4-dihydro-2-methyl-4-oxoquinazolin-6-ylmethyl)-N-(prop-2-ynyl)amino]benzoyl-L-γ-glutamyl-D-phenylalanine.

(1) Di-tert-butyl-L-γ-glutamyl-D-phenylalanine.

N-benzyloxycarbonyl-D-phenylalanine (2.99 g) was dissolved in dichloromethane (83 ml) in a 500 ml pressure bottle. To this solution concentrated sulphuric acid (0.37 ml) was added followed by liquid isobutylene (41 ml) at −20° C. The resulting solution was shaken at room temperature for 28 hours and then neutralised with a saturated solution of sodium bicarbonate. Ethyl acetate (150 ml) was added, the two layers separated and the aqueous layer washed with more ethyl acetate (1×100 ml). The combined organic extracts were then washed successively with a saturated solution of sodium bicarbonate (2×100 ml) and water (2×100 ml). After drying over magnesium sulphate the solvent was concentrated in vacuo to give a white solid. This was purified by chromatography on a silica gel column using 5% ethyl acetate in dichloromethane as eluant. There was thus obtained tert-butyl-N-benzyloxycarbonyl-D-phenylalanine (2.53 g), m.p. 80°–81° C.

NMR Spectrum (CD$_3$SOCD$_3$): 1.33 (s, 9H, C(CH$_3$)$_3$), 2.90 (bd m, 2H, β-CH$_2$), 4.13 (m, 1H, α-CH), 4.99 (m, 2H, ArCH$_2$O), 7.29 (m, 10H, 2×Ar), 7.72 (d, J=7.7 Hz, 1H, NH). Mass Spectrum (C.I.): m/e 356 (M+H)+. Elemental Analysis: Found C, 70.80; H, 7.02; N, 3.91%. C$_{21}$H$_{25}$NO$_4$ requires: C, 70.96; H, 7.09; N, 3.94%.

A solution of the product (2.45 g) in ethyl acetate (220 ml) containing 10% Pd/C (0.26 g) was stirred under hydrogen for 15 hours. The catalyst was removed by filtration and the filtrate concentrated in vacuo, yielding tert-butyl-D-phenylalanine (1.50 g). To a stirred solution of α-tert-butyl-N-benzyloxycarbonyl-L-glutamate (1.051 g) and N-methylmorpholine (0.315 g) in dry tetrahydrofuran (5 ml) cooled to −20° C. was added isobutyl chloroformate (0.424 g). After 10 minutes a solution of tert-butyl-D-phenylalanine (0.69 g) in dry tetrahydrofuran (5 ml) was added. Stirring was continued for 10 minutes at −20° C., and then at room temperature for 2 hours. N-Methylmorpholine hydrochloride was filtered off and the filtrate concentrated in vacuo. The residue was purified by chromatography on a silica gel column using a gradient (10% ethyl acetate in dichloromethane and 20% ethyl acetate in dichloromethane) as eluant. There was thus obtained di-tert-butyl-[N-(benzyloxycarbonyl)-L-γ-glutamyl]-D-phenylalanine (1.45 g), m.p. 79°–80° C.

NMR Spectrum (CD$_3$SOCD$_3$), 1.31, 1.38 (2×s, 18H, 2×C(CH$_3$)$_3$), 1.69, 1.85 (2×m, 2H, glu β-CH$_2$), 2.16 (t, J=7.0 Hz, 2H, glu γ-CH$_2$), 2.90 (m, 2H, phe β-CH$_2$), 3.87 (m, 1H, glu α-CH), 4.32 (m, 1H, phe α-CH), 5.02 (m, 2H, ArCH$_2$OCO), 7.23 (m, 5H, phe β-CH$_2$Ar), 7.35 (m, 5H, ArCH$_2$OCO), 7.62 (d, J=7.7 Hz, 1H, glu NH), 8.24 (d, J=7.7 Hz, 1H, phe NH). Mass Spectrum (C.I.) m/e 541 (M+H)+. Elemental Analysis: Found C, 66.61; H, 7.50; N, 5.13%. $C_{30}H_{40}N_2O_7$ requires C, 66.65; H, 1.46; N, 5.18%.

A solution of di-tert-butyl-N-[N-(benzyloxycarbonyl)-L-γ-glutamyl]-D-phenylalanine (0.700 g) in ethyl acetate (90 ml) containing 10% Pd/C (0.096 g) was stirred under hydrogen for 2.5 hours. The catalyst was removed by filtration and the filtrate concentrated in vacuo, yielding di-tert-butyl-L-γ-glutamyl-D-phenylalanine (0.514 g).

(2) N-p-[N-(3,4-dihydro-2-methyl-4-oxoquinazolin-6-ylmethyl)-N-(prop-2-ynyl)amino]benzoyl-L-γ-glutamyl-D-phenylalanine.

The process described in Example 1(3) was repeated using di-tert-butyl-L-γ-glutamyl-D-phenylalanine (0.447 g) in place of tri-tert-butyl-L-γ-glutamyl-D-glutamate. There was thus obtained di-tert-butyl-N-p-[N-(3,4-dihydro-2-methyl-4-oxoquinazolin-6-ylmethyl)-N-(prop-2-ynyl)amino]benzoyl-L-γ-glutamyl-D-phenylalanine (containing 1.5 equivalents of water; 0.377 g), m.p. 115°–117.5° C.

NMR Spectrum ($CD_3SOCD_3$): 1.29, 1.39 (2×s, 18H, 2×C($CH_3$)$_3$), 1.92 (m, 2H, glu β-$CH_2$), 2.20 (t, J=7.3 Hz, 2H, glu γ-$CH_2$), 2.32 (s, 3H, quinazoline 2-$CH_3$), 2.89 (m, 2H, phe β-$CH_2$Ar), 3.23 (s, 1H, C≡CH), 4.33 (m, 4H, $CH_2$C≡C, glu α-CH and phe α-CH), 4.78 (s, 2H, quinazoline 6-$CH_2$), 6.83 (d, J=8.6 Hz, 2H, 3′,5′ArH), 7.20(m, 5H, phe Ar), 7.54 (d, J=8.4 Hz, quinazoline 8-H), 7.71 (t, J=8.6 Hz, 3H, 2′,6′-ArH and quinazoline 7-H), 7.96 (s, 1H, quinazoline 5-H), 8.28 (t, J=7.0 Hz, 2H, glu NH and phe NH), 12.19 (s, 1H, lactam NH). Mass Spectrum (positive ion FAB): m/e 736 (M+H)+. Elemental Analysis: Found C, 66.06; H, 6.59; N, 8.88%. $C_{24}H_{49}N_5O_7$.1.5 $H_2O$ requires: C, 66.12; H, 6.87; N, 9.17%.

Di-tert-butyl-N-p-[N-(3,4-dihydro-2-methyl-4-oxoquinazolin-6-ylmethyl)-N-(prop-2-ynyl)amino]benzoyl-L-γ-glutamyl-D-phenylalanine (0.208 g) was treated with trifluoroacetic acid as described Example 1(3). There was thus obtained N-p-[N-(3,4-dihydro-2-methyl-4-oxoquinazolin-6-ylmethyl)-N-(prop-2-ynyl)amino]benzoyl-L-γ-glutamyl-D-phenylalanine (containing 1 equivalent of trifluoroacetic acid and 0.7 equivalents of water; 0.193 g), m.p. 130° C. (decomp).

NMR Spectrum ($CD_3SOCD_3$): 1.92 (bd m, 2H, glu β-$CH_2$), 2.17 (t, J=7.3 Hz, 2H, glu γ-$CH_2$), 2.4](s, 3H, quinazoline 2-$CH_3$), 2.81 (dd, $J_1$=13.6 Hz, $J_2$=9.8 Hz, 1H) and 3.02 (dd, $J_1$=13.6 Hz, $J_2$=4.9 Hz, 1H, Ar$CH_2$), 3.24 (s, 1H, C≡CH), 4.35 (m, 4H, $CH_2$C≡C, glu α-CH and phe α-CH), 4.81 (s, 2H, quinazoline 6-$CH_2$), 6.82 (d, J=8.8 Hz, 2H, 3′,5′ArH), 7.21 (m, 5H, phe Ar), 7.58 (d, J=8.4 Hz, 1H, quinazoline 8-H), 7.74 (m, 3H, 2′,6′-ArH and quinazoline 7-H), 8.00 (s, 1H, quinazoline 5-H), 8.22 (d, J=8.0 Hz, 1H, amidic NH), 8.29 (d, J=7.4 Hz, 1H, amidic NH). Mass Spectrum (positive ion FAB): m/e 624 (M+H)+. Elemental Analysis: Found C, 57.41; H, 4.77; N, 9.41; F, 7.77%. $C_{34}H_{33}N_5O_7.CF_3COOH.0.7 H_2O$ requires: C, 57.63; H, 4.75; N, 9.33; F, 7.60%.

Example 5

N-p-[N-(3,4-dihydro-2,7-dimethyl-4-oxoquinazolin-6-ylmethyl)-N-(prop-2-ynyl)amino]benzoyl-L-γ-glutamyl-D-glutamic acid.

The process described in Example 1(3) was repeated using p-[N-(3,4-dihydro-2,7-dimethyl-4-oxoquinazolin-6-ylmethyl)-N-(prop-2-ynyl)amino]benzoic acid, trifluoroacetate salt [0.475 g; the preparation of which is described in Example 10 of UK Patent 2 202 847B] as starting material in place of N-p-[N-(3,4-dihydro-2-methyl-4-oxoquinazolin-6-ylmethyl)-N-(prop-2-ynyl)amino]benzoic acid, trifluoroacetate salt. There was thus obtained tri-tert-butyl-N-p-[N-(3,4-dihydro-2,7-dimethyl-4-oxoquinazolin-6-ylmethyl)-N-(prop-2-ynyl)amino]benzoyl-L-γ-glutamyl-D-glutamate (containing 0.5 equivalents of water; 0.460 g), m.p. 159°–161.5° C.

NMR Spectrum ($CD_3SOCD_3$): 1.37, 1.40 (2×s, 27H, 3×C($CH_3$)$_3$), 1.71, 1.90 (2×m, 4H, 2×β-$CH_2$), 2.24 (t, J=7.0 Hz, 4H, 2×γ-$CH_2$), 2.31, 2.44 (2×s, 6H, quinazoline 2-$CH_3$ and quinazoline 7-$CH_3$), 3.21 (s, 1H, C≡CH), 4.06 (m, 1H, glu$_D$ α-CH), 4.28 (m, 3H, $CH_2$C≡C and glu$_L$ α-CH), 4.67 (s, 2H, quinazoline 6-$CH_2$), 6.80 (d, J=7.9 Hz, 2H, 3′,5′-ArH) 7.43 (s 1H, quinazoline 8-H) 7.72 (s, 1H, quinazoline 5-H), 7.75 (d, J=7.6 Hz, 2H, 2′,6′-ArH), 8.16 (d, J=7.3 Hz, 1H, glu$_D$ NH), 8.34 (d, J=7.1 Hz, 1H, glu$_L$ NH) 12.09 (s, 1H, lactam NH). Mass Spectrum (positive ion FAB): m/e 810 (M+Na)+. Elemental Analysis: Found C, 64.91; H, 7.34; N, 8.80%. $C_{43}H_{57}O_9N_5.0.5H_2O$ require: C, 64.81; H, 7.34; N, 8.79%.

Tri -tert-butyl-N-D-[N-(3,4-dihydro-2,7-dimethyl-4-oxoquinazolin-6-ylmethyl)-N-(prop-2-ynyl)amino]benzoyl-L-γ-glutamyl-D-glutamate (0.218 g) was treated with trifluoroacetic acid as described Example 1(3). There was thus obtained N-p-[N-(3,4-dihydro-2,7-dimethyl-4-oxoquinazolin-6-ylmethyl)-N-(prop-2-ynyl)amino]benzoyl-L-γ-glutamyl-D-glutamic acid (containing 1 equivalent of trifluoroacetic acid, 0.5 equivalents of diethyl ether and 1.3 equivalents of water; 0.198 g), m.p. 160° C. (decomp).

NMR Spectrum ($CD_3SOCD_3$): 1.74, 1.91 (2×m, 4H, 2×β-$CH_2$), 2.23 (m, 4H, 2×γ-$CH_2$), 2.42, 2.48 (2×s, 6H, quinazoline 2-$CH_3$ and quinazoline 7-$CH_3$), 3.22 (s, 1H, C≡CH), 4.18 (m, 1H, glu$_D$ α-CH), 4.31 (m, 3H, $CH_2$C≡C and glu$_L$ α-CH), 4.71 (s, 2H, quinazoline 6-$CH_2$), 6.80 (d, J=8.6 Hz, 2H, 3′,5′-ArH), 7.47 (s, 1H, quinazoline 8-H), 7.76 (d J=8.7 Hz 3H, quinazoline 5-H and 2′,6′-ArH) 8.15 (d, J=7.6 Hz, 1H, glu$_D$ NH), 8.34 (d, J=7.4 Hz, 1H, glu$_L$NH). Mass Spectrum (positive ion FAB): m/e 642 (M+Na)+. Elemental Analysis: Found C, 53.00; H, 5.41; N, 8.65; F, 7.10%. $C_{31}H_{33}N_5O_9.CF_3COOH.0.5(C_2H_5)_2O.1.3H_2O$ requires: C, 52.94; H, 5.28; N, 8.82; F, 7.18%.

Example 6

N-p-[N-(3,4-dihydro-2-methyl-4-oxoquinazolin-6-ylmethyl)-N-(prop-2-ynyl)amino]-o-fluorobenzoyl-L-γ-glutamyl-D-glutamic acid.

The process described in Example 1(3) was repeated using p-[N-(3,4-dihydro-2-methyl-4-oxoquinazolin-6-ylmethyl)-N-(prop-2-ynyl)amino]-o-fluorobenzoic acid, trifluoroacetate salt, m.p.>300° C. [0.479 g; prepared by an analogous procedure to that described in Example 1(2) using tert-butyl p-N-(prop-2-ynyl)amino-o-fluorobenzoate which is obtained by the reaction of tert-butyl p-amino-o-fluorobenzoate with propargyl bromide] as starting material in place of p-[N-(3,4-dihydro-2-methyl-4-oxoquinazolin-6-ylmethyl)-N-(prop-2-ynyl)amino]benzoic acid, trifluoroacetate salt. There was thus obtained tri-tert-butyl-N-p-[N-(3,4-dihydro-2-methyl-4-oxo-quinazolin-6-ylmethyl)-N-(prop-2-ynyl)amino]-o-fluorobenzoyl-L-γ-glutamyl-D-glutamate (containing 0.5 equivalents of water; 0.650 g), m.p. 105°–108° C.

NMR Spectrum ($CD_3SOCD_3$): 1.37, 1.40,(2×s, 27H, 3×C($CH_3$)$_3$), 1.70, 1.88 (2×m, 4H, 2×β-$CH_2$), 2.22 (m, 4H, 2×γ-$CH_2$), 2.32 (s, 3H, quinazoline 2-$CH_3$), 3.26 (s, 1H, C≡CH), 4.11 (m, 1H, glu_D α-CH), 4.25 (m, 1H, glu_L α-CH), 4.36 (s, 2H, CH_2C≡C), 4.79 (s, 2H, quinazoline 6-CH_2), 6.65 (m,2H, 3',5'-ArH), 7.52 (t, J=9.0 Hz, 2H, quinazoline 8-H and 6'-ArH), 7.68 (d, J=8.4 Hz, 1H, quinazoline 7-H), 7.95 (m, 2H, quinazoline 5-14 and glu_L NH), 8.14 (d, J=7.6 Hz, 1H, glu_D NH), 12.20 (s, 1H, lactam NH). Mass Spectrum (positive ion FAB): m/e 814 (M+Na)+. Elemental Analysis: Found C, 63.09; 14, 6.93; N, 8.58; F, 2.32%. C_42H_54N_5O_9F.0.5H_2O requires: C, 62.98; H, 6.93; N, 8.74; F, 2.37%.

Tri-tert-butyl-N-p-[N-(3,4-dihydro-2-methyl-4-oxoquinazolin-6-ylmethyl)-N-(prop-2-ynyl)amino]-o-fluorobenzoyl-L-γ-glutamyl-D-glutamate (0.247 g) was treated with trifluoroacetic acid as described in Example 1(3). There was thus obtained N-p-[N-(3,4-dihydro-2-methyl-4-oxoquinazolin-6-ylmethyl)-N-(prop-2-ynyl)amino]-o-fluorobenzoyl-L-γ-glutamyl-D-glutamic acid (containing 1.5 equivalents of trifluoroacetic acid, 0.6 equivalents diethyl ether and 0.5 equivalents of water; 0.170 g), m.p. 115° C.(decomp).

NMR Spectrum (CD_3SOCD_3): 1.74, 1.91 (2×m, 4H, 2×β-CH_2), 2.22 (m, 4H, 2×γ-CH_2), 2.45 (s, 3H, quinazoline 2-CH_3), 3.27(s, 1H, C≡CH), 4.16 (m, 1H, glu_D α-CH), 4.38 (m, 3H, CH_2C≡C and glu_L α-CH), 4.84 (s, 2H, quinazoline 6-CH_2), 6.66 (m, 2H, 3',5'-ArH) 7.57 (m, 2H, quinazoline 8-H and 6'-ArH), 7.79 (d, J=8.6 Hz, 1H, quinazoline 7-H), 8.01 (m, 2H, quinazoline 5-H and glu_L NH), 8.15 (d, J=7.6 Hz, 1H, glu_D NH). Mass Spectrum (positive ion FAB): m/e 646 (M+Na)+. Elemental Analysis: Found C, 50.06; H, 4.73; N, 8.04; F, 12.02%. C_30H_30N_5O_9F.1.5CF_3COOH.0.6(C_2H_5)_2O.0.5-H_2O requires: C, 50.13; H, 4.58; N, 8.25; F, 12.32%.

Example 7

N-p-[N-(3,4-dihydro-2,7-dimethyl-4-oxoquinazolin-6-ylmethyl)-N-(prop-2-ynyl)amino]-o-fluorobenzoyl-L-γ-glutamyl-D-glutamic acid.

The process described in Example 1(3) was repeated using p-[N-(3,4-dihydro-2,7-dimethyl-4-oxoquinazolin-6-ylmethyl)-N-(prop-2-ynyl)amino]-o-fluorobenzoic acid, trifluoroacetate salt [0.493 g; prepared by an analogous procedure to that described in Example 14 of UK Patent Application 2 244 708A but using 6-bromomethyl-3,4-dihydro-2,7-dimethylquinazolin-4-one] as starting material in place of p-[N-(3,4-dihydro-2-methyl-4-oxoquinazolin-6-ylmethyl)-N-(prop-2-ynyl)amino]benzoic acid, trifluoroacetate salt. There was thus obtained tri-tert-butyl-N-p-[N-(3,4-dihydro-2,7-dimethyl-4-oxoquinazolin-6-ylmethyl)-N-(prop-2-ynyl)amino]-o-fluorobenzoyl-L-γ-glutamyl-D-glutamate (containing 0.5 equivalents of water; 0.660 g), m.p. 149.5°–150.5° C.

NMR Spectrum (CD_3SOCD_3): 1.37, 1.40 (2×s, 27H, 3×C(CH_3)_3), 1.71, 1.88 (2×m, 4H, 2×β-CH_2), 2.23 (m, 4H,2×γ-CH_2), 2.30, 2.43 (2×s, 6H, quinazoline 2-CH_3 and 7-CH_3), 3.25 (s, 1H, C≡CH), 4.09 (m, 1H, glu_D α-CH), 4.30 (m, 3H, CH_2C≡C and glu_L α-CH), 4.69 (s, 2H, quinazoline 6-CH_2), 6.65 (m, 2H, 3',5'-ArH), 7.44 (s, 1H, quinazoline 8-H), 7.54 (t, J=8.6 Hz, 1H, 6'-ArH), 7.69 (s, 1H, quinazoline 5-H), 8.01 (t, J=6.5 Hz, 1H, glu_L NH), 8.14 (d, J=7.5 Hz, 1H, glu_D NH), 12.10 (s, 1H, lactam NH). Mass Spectrum (positive ion FAB): m/e 828 (M+Na)+. Elemental Analysis: Found C, 63.37; H, 6.93; N, 8.59; F, 2.51%. C_43H_56N_5O_9F.0.5H_2O requires: C, 63.38; H, 7.00; N, 8.59; F, 2.33%.

Tri-tert-butyl-N-p-[N-(3,4-dihydro-2,7-dimethyl-4-oxoquinazolin-6-ylmethyl)-N-(prop-2-ynyl)amino]-o-fluorobenzoyl-L-γ-glutamyl-D-glutamate (0.243 g) was treated with trifluoroacetic acid as described in Example 1(3). There was thus obtained N-p-[N-(3,4-dihydro-2,7-dimethyl-4-oxoquinazolin-6-ylmethyl)-N-(prop-2-ynyl)amino]-o-fluorobenzoyl-L-γ-glutamyl-D-glutamic acid (containing 1 equivalent of trifluoroacetic acid, 0.5 equivalents of diethyl ether and 0.6 equivalents of water; 0.220 g), m.p. 155° C. (decomp).

NMR Spectrum (CD_3SOCD_3): 1.73, 1.91 (2×m, 4H, 2×β-CH_2), 2.04 (m, 4H, 2×γ-CH_2), 2.41, 2.47 (2×s, 6H, quinazoline 2-CH_3 and 7-CH_3), 3.26 (s, 1H, C≡CH), 4.16 (m, 1H, glu_D α-CH), 4.33 (s, 3H, CH_2C≡C and glu_L α-CH), 4.73 (s, 2H, quinazoline 6-CH_2), 6.62 (m, 2H 3',5'-ArH) 7.47 (s 1H, quinazoline 8-H), 7.57 (t, J=8.7 Hz, 1H, 6'-ArH), 7.71 (s, 1H, quinazoline 5-H). 8.00 (t, J=6.4 Hz, 2H, glu_L NH), 8.15 (d, J=8.2 Hz, 1H, glu_D NH) Mass Spectrum (positive ion FAB): m/e 660 (M+Na)+. Elemental Analysis: Found C, 52.62; H, 5.09; N, 8.74; F, 9.14%. C_3132N_5O_9F.CF_3COOOH.0.5(C_2H_5)_2O.0.6H_2O requires: C, 52.58; H, 4.94; N, 8.76; F, 9.14%.

Example 8

N-p-[N-(3,4-dihydro-2-methyl-4-oxoquinazolin-6-ylmethyl)-N-ethylamino]benzoyl-L-γ-glutamyl-D-glutamic acid.

The process described in Example 1(3) was repeated using p-[N-(3,4-dihydro-2-methyl-4-oxoquinazolin-6-ylmethyl)-N-ethylamino]benzoic acid, trifluoroacetate salt [0.466 g; the preparation of which is described in Example 2 of UK Patent Application 2 227 016A] as starting material in place of N-p-[N-(3,4-dihydro-2-methyl-4-oxoquinazolin-6-ylmethyl)-N-(prop-2-ynyl)amino]benzoic acid, trifluoroacetate salt. There was thus obtained tri-tert-butyl-N-p-[N-(3,4-dihydro-2-methyl-4-oxoquinazolin-6-ylmethyl)-N-ethyl-amino]-benzoyl-L-γ-glutamyl-D-glutamate (containing 0.5 equivalents of water; 0.394 g), m.p. 110.5°–113.5° C.

NMR Spectrum (CD_3SOCD_3): 1.16, (t, J=6.8 Hz, 3H, N10-CH_2CH_3), 1.37, 1.39 (2×s, 27H, 3×C(CH_3)_3), 1.72, 1.89 (2×m, 4H, 2×β-CH_2), 2.23, (m, 4H, 2×γ-CH_2), 2.32 (s, 3H, quinazoline 2-CH_3), 3.57 (q, J=6.8 Hz, 2H, N10-CH_2CH_3), 4.11 (m, 1H, glu_D α-CH), 4.26 (m, 1H, glu_L α-CH), 4.73 (s, 2H, quinazoline 6-CH_2), 6.70 (d, J=8.8 Hz, 2H, 3',5'-ArH), 7.54 (d, J=8.4 Hz, 1H, quinazoline 8-H), 7.63 (d, J=8.4 Hz, 1H, quinazoline 7-H), 7.70 (d, J=8.7 Hz, 2H, 2',6'-ArH), 7.88 (s, 1H, quinazoline 5-H), 8.10 (d, J=7.5 Hz, 1H, glu_D NH), 8.18 (d, J=7.3 Hz, 1H, glu_L NH), 12.14 (s, 1H, lactam NH). Mass Spectrum (positive ion FAB): m/e 763 (M+Na)+. Elemental Analysis: Found C, 63.92; H, 7.55; N, 8.74%. C_41H_57N_5O_9.0.5H_2O requires: C, 63.71; H, 7.56; N, 9.06%.

Tri-tert-butyl-N-p-[N-(3,4-dihydro-2-methyl-4-oxoquinazolin-6-ylmethyl)-N-ethylamino]benzoyl-L-γ-glutamyl-D-glutamate (0.210 g) was treated with trifluoroacetic acid as described in Example 1(3). There was thus obtained N-p-[N-(3,4-dihydro-2-methyl-4-oxoquinazolin-6-ylmethyl)-N-ethylamino]benzoyl-L-γ-glutamyl-D-glutamic acid (containing 0.95 equivalents of trifluoroacetic acid, 0.15 equivalents of diethyl ether and 1.3 equivalents of water; 0.165 g), m.p. 140° C. (decomp).

NMR Spectrum (CD_3SOCD_3): 1.17 (t, J=6.2 Hz, 3H, N10-CH_2CH_3), 1.15, 1.95 (2×m, 4H, 2×β-CH_2), 2.25 (m, 4H, 2×γ-CH_2), 2.39 (s, 3H, quinazoline 2-CH_3), 3.58 (q, J=6.9 Hz, 2H, N10-CH_2CH_3), 4.19 (m, 1H, glu_D α-CH), 4.33 (m, 1H, glu_L α-CH), 4.15 (s, 2H, quinazoline 6-CH_2), 6.71 (d, J=8.9 Hz, 2H, 3',5.-ArH), 7.58 (d, J=8.4 Hz, 1H, quinazoline 8-H), 7.70 (m, 3H, quinazoline 7-H and 2',6'-ArH), 7.90 (s, 1H, quinazoline 5-H), 8.09 (d, J=1.8 Hz, 1H, glu$_D$ NH), 8.18 (d, J=7.5 Hz, 1H, glu$_L$ NH) Mass Spectrum (positive ion FAB): m/e 596 (M+Na)$^+$. Elemental Analysis: Found C, 51.34; H, 5.03; N, 9.39; F, 7.12%. $C_{29}H_{33}N_5O_9.0.95CF_3COOH.0.15(C_2H_5)_2O.1.3H_2O$ requires: C, 51.23; H, 5.19; N, 9.48; F, 7.33%.

Example 9

N-p-[N-(3,4-Dihydro-2-methyl-4-oxoquinazolin-6-ylmethyl)-N-methylamino]benzoyl-L-γ-glutamyl-D-glutamic acid.

The process described in Example 1(3) was repeated using p-[N-(3,4-dihydro-2-methyl-4-oxoquinazolin-6-ylmethyl)-N-methylamino]benzoic acid, trifluoroacetate salt [0.466 g; the preparation of which is described in Example 8 of UK Patent Application 2 227 016A] as starting material in place of p-[N-(3,4-dihydro-2-methyl-4-oxoquinazolin-6-ylmethyl)-N-(prop-2-ynyl)-amino]benzoic acid, trifluoroacetate salt. There was thus obtained tri-tert-butyl-N-p-[N-(3,4-dihydro-2-methyl-4-oxoquinazolin-6-ylmethyl)-N-methylamino]-benzoyl-L-γ-glutamyl-D-glutamate (0.480 g), m.p. 104.5°–108.5° C.

NMR Spectrum (CD$_3$SOCD$_3$): 1.45, 1.47 (2×s, 27H, 3×C(CH$_3$)$_3$), 1.72, 1.91 (2×m, 4H, 2×β-CH$_2$), 2.23 (m, 4H, 2×γ-CH$_2$), 2.32 (s, 3H, quinazoline 2-CH$_3$), 3.12 (s, 1H, C≡CH), 3.16 (s, 3H, N10-CH$_3$), 4.12 (m, 1H, glu$_D$ α-CH), 4.27 (m, 1H, glu$_L$ α-CH), 4.77 (s, 2H, quinazoline 6-CH$_2$), 6.75 (d, J=8.9 Hz, 2H, 3',5'-ArH), 7.53 (d, J=8.4 Hz, 1H, quinazoline 8-H), 7.61 (dd, J$_1$=8.3 Hz, J$_2$=1.9 Hz, 1H, quinazoline 7-H), 7.72 (d, J=8.7 Hz, 2H, 2',6'-ArH), 7.86 (s, 1H, quinazoline 5-H), 8.09 (d, J=7.5 Hz, 1H, glu$_D$ NH), 8.19 (d, J=7.3 Hz, 1H, glu$_L$ NH), 12.12 (s, 1H, lactam NH). Mass Spectrum (positive ion FAB): m/e 750 (M+H)$^+$. Elemental Analysis: Found C, 63.88; H, 7.50; N, 9.10%. $C_{40}H_{55}N_5O_9$ requires: C, 64.07; H, 7.39; N, 9.34%.

Tri-tert-butyl-N-p-[N-(3,4-dihydro-2-methyl-4-oxoquinazolin-6-ylmethyl)-N-methylamino]benzoyl-L-γ-glutamyl-D-glutamate (0.210 g) was treated with trifluoroacetic acid as described in Example 1(3). There was thus obtained N-p-[N-(3,4-dihydro-2-methyl-4-oxoquinazolin-6-ylmethyl)-N-methylamino]benzoyl-L-γ-glutamyl-D-glutamic acid (containing 1.5 equivalents of trifluoroacetic acid, 0.55 equivalents of diethyl ether and 1.1 equivalents of water; 0.160 g), m.p. 105° C. (decomp).

NMR Spectrum (CD$_3$SOCD$_3$): 1.75, 1.95 (2×m, 4H, 2×α-CH$_2$), 2.25 (m, 4H, 2×γ-CH$_2$), 2.41 (s, 3H, quinazoline 2-CH$_3$), 3.12 (s, 3H, N10-CH$_3$), 4.19 (m, 1H, glu$_D$ α-CH), 4.33 (m, 1H, glu$_L$ α-CH), 4.80 (s, 2H, quinazoline 6-CH$_2$), 6.76 (d, J=9.0 Hz, 2H, 3'5'-ArH), 7.57 (d, J=8.4 Hz, 1H, quinazoline 8-H), 7.67 (dd, J$_1$=8.4 Hz, J$_2$=1.9 Hz, 1H, quinazoline 7-H), 7.73 (d, J=8.8 Hz, 2H, 2',6'-ArH), 7.89 (d, J=1.5 Hz, 1H, quinazoline H-5), 8.09 (d, J=7.7 Hz, 1H, glu$_D$ NH), 8.20 (d, J=7.5 Hz, 1H, glu$_L$ NH). Mass Spectrum (positive ion FAB): m/e 582 (M+H)$^+$. Elemental Analysis: Found C, 49.27; H, 5.10; N, 8.41; F, 10.24%. $C_{28}H_{31}N_5O_9.1.5CF_3COOH.0.55(C_2H_5)_2O.1.1H_2O$ requires: C, 49.04; H, 4.92; N, 8.61; F, 10.51%.

Example 10

N-p-[N-(3,4-dihydro-2-methyl-4-oxoquinazolin-6-ylmethyl)-N-(prop-2-ynyl)amino]benzoyl-D-γ-glutamyl-D-glutamic acid.

(1) Tri-tert-butyl -D-γ-glutamyl-D-glutamate

The process described in Example 1(1) was repeated using α-tert-butyl-N-benzyloxycarbonyl-D-glutamate [2.022 g; prepared according to the procedure for α-tert-butyl-N-benzyloxycarbonyl-L-glutamate (Org. Prep. Proc. Int., 1985, 17, 416)] as starting material in place of α-tert-butyl-N-benzyloxycarbonyl-L-glutamate. There was thus obtained tri-tert-butyl-N-[N-(benzyloxycarbonyl)-D-γ-glutamyl]-D-glutamate (1.50 g), m.p. 84°–86° C.

NMR Spectrum (CD$_3$SOCD$_3$): 1.38 (s, 27H, 3×C(CH$_3$)$_3$), 1.72, 1.89 (2×m, 4H, 2×β-CH$_2$), 2.26 (m, 4H, 2×γ-CH$_2$), 3.89 (m, 1H, ZNHCH), 4.10 (m, 1H, CH$_2$CONHCH), 5.03 (m, 2H, ArCH$_2$), 7.35 (m, 5H, Ar), 7.64 (d, J=7.7 Hz, 1H, ZNHCH), 8.12 (d, J=7.4 Hz, 1 H, CH$_2$CONHCH). Mass Spectrum (positive ion FAB): m/e 579 (M+H)$^+$. Elemental Analysis: Found C, 62.21; H, 7.98; N, 4.80%. $C_{30}H_{46}N_2O_9$ requires: C, 62.27; H, 8.01; N, 4.84%.

A solution of tri-tert-butyl-N-[N-(benzyloxycarbonyl)-D-γ-glutamyl]-D-glutamate (0.718 g) in ethyl acetate (90 ml) containing 10% Pd/C (0.1 g) was stirred under hydrogen for 2 hours. The catalyst was removed by filtration and the filtrate concentrated in vacuo, yielding tri-tert-butyl-D-γ-glutamyl-D-glutamate (0.460 g)

(2) N-p-[N-(3,4-Dihydro-2-methyl-4-oxoquinazolin-6-ylmethyl)-N-(prop-2-ynyl)amino]benzoyl-D-γ-glutamyl-D-glutamic acid.

The process described in Example 1(3) was repeated using tri-tert-butyl-D-γ-glutamyl-D-glutamate (0.444 g) as starting material in place of tri-tert-butyl-L-γ-glutamyl-D-glutamate. There was thus obtained tri-tert-butyl-N-p-[N-(3,4-dihydro-2-methyl-4-oxoquinazolin-6-ylmethyl)-N-(prop-2-ynyl)amino]benzoyl-D-γ-glutamyl-D-glutamate, (0.400 g), m.p. 110°–116° C.

NMR Spectrum (CD$_3$SOCD$_3$): 1.37, 1.39 (2×s, 27H, 3×C(CH$_3$)$_3$), 1.71, 1.89 (2×m, 4H, 2×α-CH$_2$), 2.24 (m, 4H, 2×γ-CH$_2$), 2.33 (s, 3H, quinazoline 2-CH$_3$), 3.23 (s, 1H, C≡CH), 4.10 (m, 1H, CH$_2$CONHCH), 4.24 (m, 1H, —C$_6$H$_4$—CONHCH), 4.34 (s, 2H, CH$_2$C≡C), 4.78 (s, 2H, quinazoline 6-CH$_2$), 6.83 (d, J=3 8.7 Hz, 2H, 3',5'-ArH), 7.54 (d, J=8.4 Hz, 1H, quinazoline 8-H), 7.72 (m, 3H, quinazoline 7-H and 2',6'-ArH), 7.96 (s, 1H, quinazoline 5-H), 8.13 (d, J=7.5 Hz, 1H, CH$_2$CONHCH), 8.32 (d, J=7.4 Hz, 1H, —C$_6$H$_4$—CONH), 12.19 (s, 1H, lactam NH). Mass Spectrum (positive ion FAB): m/e 773 (M$^+$). Elemental Analysis: Found C, 64.90; H, 7.27; N, 8.90%. $C_{42}H_{55}N_5O_9$ requires: C, 65.18; H, 7.16; N, 9.05%.

Tri-tert-butyl-N-p-[N-(3,4-dihydro-2-methyl-4-oxoquinazolin-6-ylmethyl)-N-(prop-2-ynyl)amino]benzoyl-D-γ-glutamyl-D-glutamate (0.208 g) was treated with trifluoroacetic acid as described in Example 1(3). There was thus obtained N-p-[N-(3,4-dihydro-2-methyl-4-oxoquinazolin-6-ylmethyl)-N-(prop-2-ynyl)amino]-benzoyl-D-γ-glutamyl-D-glutamic acid (containing 1.15.equivalents of trifluoroacetic acid and 1 equivalent of water; 0.180 g), m.p. 95=C (decomp).

NMR Spectrum (CD$_3$SOCD$_3$): 1.72, 1.74 (2×m, 4H, 2×β-CH$_2$), 2.23 (m, 4H, 2×γ-CH$_2$), 2.42 (s, 3H, quinazoline 2-CH$_3$), 3.24 (s, 1H, C≡CH), 4.18 (m, 1H, CH$_2$CONHCH), 4.36 (m, 3H, —C$_6$H$_4$—CONHCH and CH$_2$C≡C), 4.81 (s, 2H, quinazoline 6-CH$_2$), 6.83 (d, J=8.8 Hz, 2H, 3',5'-ArH), 7.60 (d, J=8.4 Hz, 1H, quinazoline 8-H), 7.77 (m, 3H, quinazoline 7-H and 2',6'-ArH), 8.00 (s, 1H, quinazoline 5-H), 8.13 (d, J=7.7 Hz, 1H, CH$_2$CONHCH), 8.33 (d, J=7.5 Hz, 1 H, —C$_6$H$_4$—CONH). Mass Spectrum (positive ion FAB): m/e 606 (M+H)$^+$. Elemental Analysis: Found C, 51.37; H, 4.52; N, 9.07; F, 8.64%. C$_{30}$H$_{31}$N$_5$O$_9$.1.15CF$_3$COOH.1-H$_2$O requires: C, 51.40; H, 4.56; N, 9.28; F, 8.68%.

Example 11

N-p-[N-(3,4-Dihydro-2,7-dimethyl-4-oxoquinazolin-6-ylmethyl)-N-methylamino]benzoyl-L-γ-glutamyl-D-glutamic acid (1) p-[N-(3,4-Dihydro-2,7-dimethyl-4-oxoquinazolin-6-ylmethyl)-N-methylamino]benzoic acid p-[N-(3,4-Dihydro-2,7-dimethyl-4-oxo-3-pivaloyloxymethylquinazolin-6-ylmethyl)-N-methylamino]benzoic acid (4.8 g) was prepared as described in Example 22 of UK Patent Application 2 244 708A.

A mixture of the product, ethanol (60 ml), water (50 ml) and 1N sodium hydroxide (30 ml) was stirred at room temperature for 1.5 hours, then acidified to pit 4 with 1N hydrochloric acid. The solid was collected by filtration and dried in vacuo over phosphorus pentoxide to yield p-[N-(3,4-dihydro-2,7-dimethyl-4-oxoquinazolin-6-ylmethyl)-N-methylamino]benzoic acid.

A mixture of the product and trifluoroacetic acid (30 ml) was stirred at room temperature for 15 minutes and then evaporated. The residue was triturated with diethyl ether (60 ml) and the brown solid filtered off and dried in vacuo, yielding the p-aminobenzoic acid as its trifluoroacetate salt (2.9 g), m.p.>270° C.

(2) N-p-[N-(3,4-Dihydro-2,7-dimethyl-4-oxoquinazolin-6-ylmethyl)-N-methylamino]benzoyl-L-γ-glutamyl-D-glutamic acid The process described in Example 1(3) was repeated using p-[N-(3,4-dihydro-2,7-dimethyl-4-oxoquinazolin-6-ylmethyl)-N-methylamino]benzoic acid, trifluoroacetate salt (0.580 g) as starting material in place of p-[N-(3,4-dihydro-2-methyl-4-oxoquinazolin-6-ylmethyl)-N-(prop-2-ynyl)amino]benzoic acid, trifluoroacetate salt. There was thus obtained tri-tert-butyl-N-p-[N-(3,4-dihydro-2,7-dimethyl-4-oxoquinazolin-6-ylmethyl)-N-methylamino]benzoyl-L-γ-glutamyl-D-glutamate (containing 0.6 equivalents of water, 0.288 g), m.p. 243.5°–245° C.

NMR Spectrum (CD$_3$SOCD$_3$); 1.37, 1.40 (2×s, 27H, 3×C(CH$_3$)$_3$), 1.83–2.03 (m, 4H, 2×α-CH$_2$), 2.23 (t, J=6.8 Hz, 4H, 2×γ-CH$_2$), 2.30 (s, 3H, quinazoline 2-CH$_3$), 2.43 (s, 3H, quinazoline 7-CH$_3$), 3.13 (s, 3H, N10-CH$_3$), 4.09 (m, 1H, glu$_D$ α-CH), 4.24 (m, 1H, glu$_L$ α-CH), 4.70 (s, 2H, quinazoline 6-CH$_2$), 6.70 (d, J=8.5 Hz, 2H, 3',5'-ArH), 7.44, 7.52 (2×s, 2H, quinazoline 5-H and quinazoline 8-H), 7.73 (d, J=8 3 Hz, 2H, 2',6'-ArH) 8.17 (d, J=7.5 Hz, 1H, glu$_D$ NH), 8,28 (d, J=7.2 Hz, 1H, glu$_L$ NH), 12.10 (s, 1H, lactam NH). Mass Spectrum: (ESI) m/e 764 (M+H)$^+$. Elemental Analysis: Found C, 63.58; H, 7.57; N, 8.97%. C$_{41}$H$_{57}$N$_5$O$_9$.0.6-H$_2$O requires C, 63.56; H, 7.57; N, 9.04%.

Tri-tert-butyl-N-p-[N-(3,4-dihydro-2,7-dimethyl-4-oxoquinazolin-6-ylmethyl)-N-methylamino]benzoyl-L-γ-glutamyl-D-glutamate (0.219 g) was treated with trifluoroacetic acid as described in Example 1(3). There was thus obtained N-p-[N-(3,4-dihydro-2,7-dimethyl-4-oxoquinazolin-6-ylmethyl)-N-methylamino]benzoyl-L-γ-glutamyl-D-glutamic acid (containing 1.1 equivalents of CF$_3$CO$_2$H, 1 equivalent of H$_2$O and 0.2 equivalents of Et$_2$O; 0.19 g), m.p.>150° C. (decomposition).

NMR Spectrum (CD$_3$SOCD$_3$): 1.70–2.09 (m, 4H; 2×β-CH$_2$), 2.25 (m, 4H, 2×γ-CH$_2$), 2.42, 2.48 (2×s, 6H, quinazoline 2-CH$_3$ and quinazoline 7-CH$_3$), 3.14 (s, 3H, N10-CH$_3$), 4.11 (m, 1H, glu$_D$ α-CH), 4.31 (m, 1H, glu$_L$ α-CH), 4.13 (s, 2H, quinazoline 6-CH$_2$), 6.71 (d, J=8.9 Hz, 2H, 3',5'-ArH) 7.48, 7.52 (2×s, 2H, quinazoline 5-H and quinazoline 8-H), 7.74 (d, J=8.9 Hz, 2H, 2',6'-ArH) 8.17 (d, J=7.7 Hz, 1H, glu$_D$ NH), 8.29 (d, J=7.5 Hz, 1H, glu$_L$ NH) Mass Spectrum: (ESI) m/e 596 (M+H)$^+$. Elemental Analysis: Found C, 50.98; H, 5.05; N, 9.12; F, 8.18%. C$_{29}$H$_{33}$N$_5$O$_9$.1.1CF$_3$CO$_2$H.H$_2$O.0-.2Et$_2$O requires C, 50.98; H, 5.09; N, 9.29; F, 8.32%.

Example 12

N-p-[N-(3,4-Dihydro-2-methyl-4-oxoquinazolin-6-ylmethyl)-N-methylamino]-N-fluorobenzoyl-L-γ-glutamyl-D-glutamic acid (1) p-[N-(3,4-Dihydro-2-methyl-4-oxoquinazolin-6-ylmethyl)-N-methylamino]-o-fluorobenzoic acid A mixture of 6-bromomethyl-3,4-dihydro-2-methyl-3-pivaloyloxy-methylquinazolin-4-one [9.2 g; prepared as described in Example 1 of UK Patent 2 188 31981], tert-butyl p-amino-o-fluorobenzoate [5.8 g; the preparation of which is described in Example 3 of UK Patent Application 2 227 016A], 2,6-lutidine (2.94 g) and dimethylacetamide (30 ml) was stirred at 95° C. for 10 hours. The dimethylacetamide was then removed in vacuo and the residue partitioned between ethyl acetate and water. The water layer was washed with ethyl acetate, and the combined organic phases washed with water and dried over magnesium sulphate, The ethyl acetate was removed in vacuo and the yellow oil purified by chromatography on a silica gel column using a gradient of ethyl acetate in hexane as eluants. There was thus obtained tert-butyl p-[N-(3,4-dihydro-2-methyl-4-oxo-3-pivaloyloxymethylquinazolin-6-ylmethyl)amino]-o-fluorobenzoate (10.3 g), m.p. 149°–150° C.

To a solution of the product (10.3 g) in glacial acetic acid (150 ml) was added 37% aqueous formaldehyde (17 ml). After stirring at laboratory temperature for 10 minutes, sodium cyanoborohydride (2.83 g) was added in one portion and the mixture was stirred for a further 1.25 hours. The acetic acid was then removed in vacuo and the residue partitioned between ethyl acetate and water. The ethyl acetate was washed with saturated sodium bicarbonate, water and then dried. The solvent was removed in vacuo and the residue purified by chromatography on a silica gel column using 30% ethyl acetate in dichloromethane as eluant to yield tert-butyl p-[N-(3,4-dihydro-2-methyl-4-oxo-3-pivaloyloxymethylquinazolin-6-ylmethyl)-N-methylamino]-N-fluorobenzoate.

A mixture of the product (6.6 g) and trifluoroacetic acid (35 ml) was stirred at laboratory temperature for 1 hour and then evaporated in vacuo. The residue was treated with diethyl ether (50 ml) and the white solid filtered off and dried in vacuo to yield p-[N-(3,4-dihydro-2-methyl-4-oxo-3-pivaloyloxymethylquinazolin-6-ylmethyl)-N-methylamino]-o-fluorobenzoic acid.

A mixture of the product (4.3 g), ethanol (200 ml), water (60 ml) and 1N sodium hydroxide (34 ml) was stirred at laboratory temperature for 34 hours, then acidified to pit 4 with 2N hydrochloric acid. The solid was collected by filtration and dried in vacuo over phosphorus pentoxide to yield p-[N-(3,4-dihydro-2- methyl-4-oxoquinazolin-6-ylmethyl)-N-methylamino]-o-fluorobenzoic acid.

A mixture of the product (1 g) and trifluoroacetic acid (40 ml) was stirred at laboratory temperature for 10 minutes and then evaporated. The residue was triturated with diethyl ether (50 ml) and the pale yellow solid filtered off and dried in vacuo to yield the p-amino-o-fluorobenzoic acid as its trifluoroacetate salt, m.p. 297°–298° C.

(2) N-p-[N-(3,4-Dihydro-2-methyl-4-oxoquinazolin-6-ylmethyl)-N-methyl amino]-o-fluorobenzoyl-L-$\gamma$-glutamyl-D-glutamic acid The process described in Example 1(3) was repeated using p-[N-(3,4-dihydro-2-methyl-4-oxoquinazolin-6-ylmethyl)-N-methylamino]-o-fluorobenzoic acid, trifluoroacetate salt (0.455 g), as starting material in place of p-[N-(3,4-dihydro-2-methyl-4-oxoquinazolin-6-ylmethyl)-N-(prop-2-ynyl)amino]benzoic acid, trifluoroacetate salt. There was thus obtained tri-tert-butyl-N-p-[N-(3,4-dihydro-2-methyl-4-oxoquinazolin-6-ylmethyl)-N-methylamino]-o-fluorobenzoyl-L-$\gamma$-glutamyl-D-glutamate (0.564 g), m.p. 100°–102° C.

NMR Spectrum (CD$_3$SOCD$_3$): 1.38, 1.41 (2×s, 27H, C(CH$_3$)$_3$), 1.72, 1.89, 2.00 (3×m, 4H, $\beta$-CH$_2$), 2.22 (t, J=6.7 Hz, 4H, $\gamma$-CH$_2$), 2.33 (s, 3H, quinazoline 2-C$_3$), 3.12 (s, 3H, N10-CH$_3$), 4.10 (m, 1H, glu$_D$ $\alpha$-CH), 4.29 (m, 1H, glu$_L$ $\alpha$-CH), 4.78 (s, 2H, quinazoline 6-CH$_2$), 6.55 (dd, J=15.4, 2.1 Hz, 1H, 3'-ArH), 6.63 (dd, J=8.9, 2.2 Hz, 1H, 5'-ArH), 7.57 (m, 3H, 6'-ArH and quinazoline 7-H and 8-H), 7.80 (t, J=6.9 Hz, 1H, glu$_L$ NH), 7.86 (s, 1H, quinazoline 5-H), 8.08 (d, J=7.6 Hz, 1H, glu$_D$ NH), 12.14 (s, lactam NH). Mass Spectrum (ESI): 768 (M+H)$^+$. Elemental Analysis: Found C, 62.70; H, 7.32; N, 8.87; F, 2.44%. C$_{40}$H$_{54}$FN$_5$O$_9$ requires C, 62.57; H, 7.09; N, 9.12; F, 2.47%.

Tri-tert-butyl-N-p-[N-(3,4-dihydro-2-methyl-4-oxoquinazolin-6-ylmethyl)-N-methylamino]-o-fluorobenzoyl-L-$\gamma$-glutamyl-D-glutamate (0.212 g), was treated with trifluoroacetic acid as described Example 1(3). There was thus obtained N-p-[N-(3,4-dihydro-2-methyl-4-oxoquinazolin-6-ylmethyl)-N-methylamino]-o-fluorobenzoyl-L-$\gamma$-glutamyl-D-glutamate (containing 1.3 equivalents of CF$_3$CO$_2$H, 0.75 equivalents of H$_2$O and 1 equivalent of Et$_2$O; 0.218 g), m.p. 145°–147° C.

NMR Spectrum (CD$_3$SOCD$_3$); 1.75, 1.92, 2.04 (3×m, 4H, $\beta$-CH$_2$), 2.23 (m, 4H, $\gamma$-CH$_2$), 2.38 (s, 3H, quinazoline 2-CH$_3$), 3.12 (s, 3H, N$_{10}$-CH$_3$), 4.17 (m, 1H, glu$_D$ $\alpha$-CH), 4.37 (m, 1H, glu$_L$ $\alpha$-CH), 4.80 (s, 2H, quinazoline 6-CH$_2$), 6.56 (dd, J=15.4, 2.1 Hz, 1H, 3'-ArH), 6.63 (dd, J=8.9, 2.2 Hz, 1H, 5'-ArH), 7.57 (m, 2H, 6'-ArH plus quinazoline 8-H), 7.64 (dd, J=8.5, 1.8 Hz, quinazoline 7-H), 7.78 (t, J=6.9 Hz, 1H, glu$_L$ NH), 7.87 (d, 1H, quinazoline 5-H), 8.08 (d, J=7.8 Hz, 1H, glu$_D$ NH), 12.40 (bd, CO$_2$H) Mass Spectrum (ESI): 600 (M+H)$^+$. Elemental Analysis: Found C, 49.77; H, 5.25; N, 8.10; F, 10.95%. C$_{28}$H$_{30}$N$_5$O$_9$F.1.3CF$_3$CO$_2$H.0.75-H$_2$O.Et$_2$O requires C, 49.74; H, 5.16; N, 8.39; F, 11.14%.

Example 13

N-p-[N-(3,4-Dihydro-2,7-dimethyl-4-oxoquinazolin-6-ylmethyl)-N-methylamino]-o-fluorobenzoyl-L-$\gamma$-glutamyl-D-glutamic acid The process described in Example 1(3) was repeated using p-[N-(3,4-dihydro-2,7-dimethyl-4-oxoquinazolin-6-ylmethyl)-N-methylamino]-o-fluorobenzoic acid, trifluoroacetate salt, m.p. 312°–314° C. (decomposition) [0.469 g; prepared by an analogous procedure to that described in Example 12(1) starting from 6-bromomethyl-3,4 -dihydro-2,7 -dimethyl-3-pivaloyloxymethyl-quinazolin-4-one, the preparation of which is described in Example 13 of UK Patent Application 2 244 708A] as starting material in place of p-[N-(3,4-dihydro-2-methyl-4-oxoquinazolin-6-ylmethyl)-N-(prop-2-ynyl)amino]-benzoic acid, trifluoroacetate salt. There was thus obtained tri-tert-butyl-N-p-[N-(3,4-dihydro-2,7-dimethyl-4-oxoquinazolin-6-ylmethyl)-N-methylamino]-o-fluorobenzoyl-L-$\gamma$-glutamyl-D-glutamate (0.572 g), m.p. 172°–173° C.

NMR Spectrum (CD$_3$SOCD$_3$): 1.37, 1.40 (2×s, 27H, C(CH$_3$)$_3$), 1.71, 1.89, 1.99 (3×m, 4H, $\beta$-CH$_2$), 2.23 (m, 4H, $\gamma$-CH$_2$), 2.31 (s, 3H, quinazoline 2-CH$_3$), 2.43 (s, 3H, quinazoline 7-CH$_3$), 3.12 (s, 3H, N10-CH$_3$), 4.08 (m, 1H, glu$_D$ $\alpha$-CH), 4.27 (m, 1H, glu$_L$ $\alpha$-CH), 4.70 (s, 2H, quinazoline 6-CH$_2$), 6.53 (d, J=14.2 Hz, 1H, 3'-ArH), 6.57 (d, J=7.9 Hz, 1H, 5'-ArH), 7.45, 7.48 (2×s, each 1H, quinazoline 8-H and 5-H), 7.54 (t, J=8.9 Hz, 1H, 6'-ArH), 7.90 (d, J=6.4Hz, 1H, glu$_L$ NH), 8.16 (d, J=7.6 Hz, 1H, glu$_D$ NH), 12.12 (s, 1H, lactam NH). Mass Spectrum (ESI): 782 (M+H)$^+$. Elemental Analysis: Found C, 62.68; 14, 7.25; N, 8.97; F, 2.42%. C$_{41}$H$_{56}$FN$_5$O$_9$ requires C, 62.98; H, 7.22; N, 8.96; F, 2.43%.

Tri-tert-butyl-N-p-[N-(3,4-dihydro-2,7-dimethyl-4-oxoquinazolin-6-ylmethyl)-N-methylamino]-o-fluorobenzoyl-L-$\gamma$-glutamyl-D-glutamate (0.20 g), was treated with trifluoroacetic acid as described in Example 1(3). There was thus obtained N-p-[N-(3,4-dihydro-2,7-dimethyl-4-oxoquinazolin-6-ylmethyl)-N-methylamino]-o-fluorobenzoyl-L-$\gamma$-glutamyl-D-glutamate (containing 1 equivalent of trifluoroacetic acid and 1 equivalent of water; 0.175g), m.p. 159°–161° C.

NMR Spectrum (CD$_3$SOCD$_3$); 1.75, 1.92, 2.04 (3×m, 4H, $\beta$-CH$_2$), 2.24 (m, 4H, $\gamma$-CH$_2$), 2.38 (s, 3H, quinazoline 2-CH$_3$), 2.45 (s, 3H, quinazoline 7-CH$_3$), 3.12 (s, 3H, N10-CH$_3$), 4.17 (m, 1H, glu$_D$ $\alpha$-CH), 4.37 (m, 1H, glu$_L$ $\alpha$-CH), 4.72 (s, 2H, quinazoline 6-CH$_2$), 6.53 (d, J=15.1 Hz, 1H, 3'-ArH), 6.58 (d, J=10.2 Hz, 1H, 5'-ArH), 7.46 (s, 1H, quinazoline 8-H), 7.52 (s, 1H, quinazoline 5-H), 7.58 (t, J=6.9 Hz, 1H, 6'-ArH), 7.80 (t, J=6.9 Hz, 1H, glu$_L$ NH), 8.10 (d, J=7.7 Hz, 1H, glu$_D$NH), 12.42 (bd, CO$_2$H). Mass Spectrum (ESI): 614 (M+H)$^+$. Elemental Analysis: Found C, 50.14; H, 4.12; N, 9.21; F, 10.24%. C$_{29}$H$_{32}$FN$_5$O$_9$.CF$_3$COOH.H$_2$O requires C, 49.93; H, 4.73; N, 9.40; F, 10.19%.

Example 14

Tests of Biological Activity

The compounds of Examples 1 and 10, the L-$\gamma$-glutamyl-D-glutamic acid and D-$\gamma$-glutamyl-D-glutamic acid derivatives, respectively, of p-[N-(3,4-dihydro-2-methyl-4-oxoquinazolin-6-ylmethyl)-N-(prop-2-ynyl-)amino]benzoic acid and, for comparative purposes, the corresponding L-$\gamma$-glutamyl-L-glutamic acid and D-$\gamma$-glutamyl-L-glutamic acid derivatives were tested for their thymidylate synthase inhibitory properties and for their ability to inhibit growth of the L1210 in tests as indicated under (a) and (b) on page 19.

The four compounds were also tested for in vivo stability to cleavage of the central amide linkage of the dipeptide. This test comprised injecting the compound intraperitoneally into male C57/DBA2 (F$_1$ hybrid) mice at a standard dosage rate of 100 mg/kg, sacrificing the animals after 1 hour, removing the plasma, liver and kidneys, homogenising these individually in nine times the volume of 0.1 M Tris HCl at pH 10, precipitating the protein and analysing the product in 0.05 M NaHCO$_3$ by hplc on a Sperisorb C-6 column eluting with acetonitrile/sodium acetate of pH 5.0. UV measurements at 280 and 313 nm were used to detect the dipeptide and the breakdown product of cleavage at the central amide bond of the dipeptide, i.e. the L-glutamic acid derivative or D-glutamic acid derivative. Identification of the parent compound and any breakdown product was effected by Rt comparisons against standard samples of these compounds which have been subjected to the same treatment as the liver, kidney and plasma samples.

The results obtained are shown in the Table, the identification of a compound which is "not cleaved" as compared with a compound which is "cleaved" being made on the basis of the amount of the dipeptide and its cleavage product found in the plasma and the liver. Thus, a typical experiment with the L-glu-D-glu compound showed, as a percentage of the total drug administered, 27±2% of the parent dipeptide present in the liver and no cleavage product, whilst a similar experiment with the L-glu-L-glu compound showed 1.6±0.8% of the parent dipeptide and 40±13% of cleavage product. The remaining part of the parent dipeptide which was detected was found mostly in the plasma for both the L-glu-D-glu and L-glu-L-glu compounds accompanied by no cleavage product in the case of the former but by a significant amount of the cleavage product in the case of the latter.

Similar tests on various other compounds of the Examples showed that in each case the compound was substantially uncleaved.

TABLE

| Dipeptide | TS IC$_{50}$ μM[1] | L1210 IC$_{50}$ μM | Stability |
|---|---|---|---|
| L-glu-D-glu | 0.0046 | 0.18 | not cleaved |
| D-glu-D-glu | 0.026 | 1.3 | not cleaved |
| L-glu-L-glu | 0.002 | 0.1 | cleaved |
| D-glu-L-glu | 0.036 | 3.4 | cleaved |

[1]The IC$_{50}$ values may be converted to inverse relative potency I$_{50}$ values by dividing the IC$_{50}$ value obtained for the compound by the IC$_{50}$ value obtained in the same experiment for the compound CB3717, this latter figure typically being 0.02 (Ki = 3 nM).

We claim:

1. A quinazoline of the formula (I):

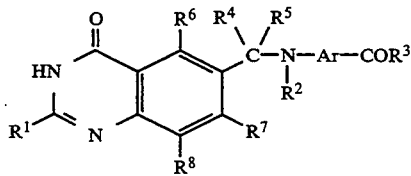

wherein R$^1$ is hydrogen or amino;
or R$^1$ is alkyl, alkoxy or alkylthio each of up to 6 carbon atoms;
or R$^1$ is aryl or aryloxy, each of up to 10 carbon atoms;
or R$^1$ is halogeno, hydroxy or mercapto;
or R$^1$ is alkyl of up to 3 carbon atoms which bears one or more substituents selected from halogeno, hydroxy and alkanoylamino each of up to 6 carbon atoms; or R$^1$ is alkoxy of up to 3 carbon atoms which bears one or more substituents selected from hydroxy and alkoxy of up to 6 carbon atoms;

wherein R$^2$ is hydrogen or alkyl, alkenyl, alkynyl, hydroxyalkyl, alkoxyalkyl, mercaptoalkyl, alkylthioalkyl, halogenoalkyl, cyanoalkyl, aminoalkyl, alkylaminoalkyl, dialkylaminoalkyl, alkanoylalkyl, carboxyalkyl, carbamoylalkyl or alkanoyl each of up to 6 carbon atoms;

wherein Ar is phenylene, thienylene, pyridylene, pyrimidinylene, thiazolylene or oxazolylene which is substituted or which bears one or more substituents selected from halogeno, cyano, nitro, hydroxy, amino and carbamoyl and alkyl, alkoxy, halogenoalkyl, alkenoylamino and alkoxycarbonyl each of up to 6 carbon atoms;

wherein R$^3$ is a grouping —NHCH(CO$_2$H)—A—CONH—CH(Y)—CO$_2$H,
in which A is an alkylene group of up to 6 carbon atoms;
and Y is alkyl, alkenyl or alkynyl each of up to 6 carbon atoms;
or Y is alkyl of up to 6 carbon atoms which bears one or more substituents selected from amino, carboxy, hydroxy and mercapto;
or Y is phenyl or benzyl;
or Y is an alternative group present in a naturally occurring amino acid H$_2$NCH(Y)CO$_2$H;
the configuration at the asymmetric carbon atom of the first amino acid residue —NHCH(CO$_2$H)—A—CO— of R$^3$ being L or D and the configuration at the asymmetric carbon atom of the second amino acid residue —NHCH(Y)—CO$_2$H of R$^3$ being D;

wherein R$^4$ is hydrogen or alkyl of up to 4 carbon atoms;

wherein R$^5$ is hydrogen or alkyl of up to 4 carbon atoms; and wherein each of R$^6$, R$^7$ and R$^8$ is hydrogen or alkyl or alkoxy each of up to 4 carbon atoms; or is halogeno;

the quinazoline optionally being in the form of a pharmaceutically acceptable salt, ester or amide thereof.

2. A quinazoline according to claim 1,
wherein R$^1$ is hydrogen, amino, methyl, ethyl, isopropyl, methoxy, ethoxy, methylthio, phenyl, tolyl, phenoxy, chloro, bromo, hydroxy, mercapto, fluoromethyl, difluoromethyl, trifluoromethyl, chloromethyl, hydroxymethyl, acetamidomethyl, 2-hydroxyethoxy, 2-methoxyethoxy or 2-ethoxyethoxy;

wherein R$^2$ is hydrogen, methyl, ethyl, propyl, prop-2-enyl, but-2-enyl, prop-2-ynyl, but-2-ynyl, 2-hydroxyethyl, 3-hydroxypropyl, 2-methoxyethyl, 3-methoxypropyl, 2-mercaptoethyl, 2-methylthioethyl, 2-fluoroethyl, 2-chloroethyl, 2-bromoethyl, 3-fluoropropyl, cyanomethyl, 2-cyanoethyl, 2-aminoethyl, 2-methylaminoethyl, 2-dimethylaminoethyl, acetonyl, carboxymethyl, carbamoylmethyl or acetyl;

wherein Ar is 1,4-phenylene, thienylene, pyridylene, pyrimidinylene, thiazolylene or oxazolylene which is unsubstituted or which bears one or two substituents selected from fluoro, chloro, bromo, phenyl, cyano, nitro, hydroxy, amino, carbamoyl, methyl, ethyl, methoxy, ethoxy, fluoromethyl, difluoromethyl, trifluoromethyl and acetamido;

wherein R$^3$ is a group of formula,

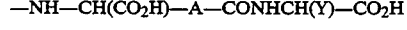

—NH—CH(CO$_2$H)—A—CONHCH(Y)—CO$_2$H in which A is as defined in claim 1; and

Y is alkyl, alkenyl or alkynyl each of up to 6 carbon atoms;

or Y is alkyl of up to 6 carbon atoms which bears one or more substituents selected from amino, carboxy, hydroxy and mercapto;

or Y is phenyl or benzyl;

wherein $R^4$ is hydrogen, methyl or ethyl;

wherein $R^5$ is hydrogen, methyl or ethyl; and wherein each of $R^6$, $R^7$ and $R^8$ is hydrogen, methyl, ethyl, methoxy, ethoxy, fluoro, chloro or bromo.

3. A quinazoline according to claim 1, wherein $R^1$ is hydrogen, amino, methyl, ethyl or methoxy;

wherein $R^2$ is methyl, ethyl, prop-2-enyl, prop-2-ynyl, 2-hydroxyethyl, 3-hydroxypropyl, 2-fluoroethyl or acetonyl;

wherein Ar is 1,4-phenylene, 2-fluoro-1,4-phenylene or 2,6-difluoro-1,4-phenylene;

wherein $R^3$ is a group of formula

—NH—CH(CO$_2$H)CH$_2$CH$_2$CONHCH(CO$_2$H)—(CH$_2$)$_m$CO$_2$H in which m is 1, 2 or 3;

wherein $R^4$ is hydrogen or methyl;

wherein $R^5$ is hydrogen;

wherein $R^6$ is hydrogen or chloro;

wherein $R^7$ is hydrogen, methyl, fluoro or chloro; and wherein $R^8$ is hydrogen, methoxy or chloro.

4. A quinazoline according to claim 1, wherein $R^1$ is amino, methyl or methoxy;

wherein $R^2$ is methyl, ethyl, prop-2-enyl, prop-2-ynyl, 2-hydroxyethyl, 3-hydroxypropyl, 2-fluoroethyl or acetonyl;

wherein Ar is 1,4-phenylene, 2-fluoro-1,4-phenylene or 2,6-difluoro-1,4-phenylene;

wherein $R^3$ is the residue of the dipeptide γ-glutamyl-aspartic acid, γ-glutamyl-glutamic acid, γ-glutamyl-2-aminoadipic acid or γ-glutamyl-alanine;

wherein $R^4$ is hydrogen or methyl;

wherein $R^5$ is hydrogen;

wherein $R^6$ is hydrogen or chloro;

wherein $R^7$ is hydrogen, methyl, fluoro or chloro; and wherein $R^8$ is hydrogen, methoxy or chloro.

5. A quinazoline according to claim 1, wherein the first, N-terminal amino acid residue —NHCH(CO$_2$H)—A—CO— has the L configuration.

6. A quinazoline according to claim 5, wherein the residue is of L-γ-glutamic acid.

7. A quinazoline according to claim 1 wherein $R^1$ is methyl;

wherein $R^2$ is methyl or prop-2-ynyl;

wherein Ar is 1,4-phenylene or 2-fluoro-1,4-phenylene;

wherein $R^3$ is the residue of L-γ-glutamyl-D-glutamic acid;

wherein $R^4$ is hydrogen or methyl;

wherein $R^5$ is hydrogen;

wherein $R^6$ is hydrogen or chloro;

wherein $R^7$ is hydrogen, methyl, methoxy, fluoro or chloro; and wherein $R^8$ is hydrogen, methyl, methoxy or chloro.

8. A compound being:

N-p-[N-(3,4-dihydro-2-amino-4-oxoquinazolin-6-ylmethyl)-N-methylamino]benzoyl-L-γ-glutamyl-D-glutamic acid, N-p-[N-(3,4-dihydro-2-amino-4-oxoquinazolin-6-ylmethyl)-N-ethylamino]benzoyl-L-γ-glutamyl-D-glutamic acid, N-p-[N-(3,4-dihydro-2-amino-4-oxoquinazolin-6-ylmethyl)-N-(prop-2-ynyl)amino]benzoyl-L-γ-glutamyl-D-glutamic acid, N-p-[N-(3,4-dihydro-2-methyl-4-oxoquinazolin-6-ylmethyl)-N-methylamino]benzoyl-L-γ-glutamyl-D-glutamic acid, N-p-[N-(3,4-dihydro-2-methyl-4-oxoquinazolin-6-ylmethyl)-N-ethylamino]benzoyl-L-γ-glutamyl-D-glutamic acid, N-p-[N-(3,4-dihydro-2-methyl-4-oxoquinazolin-6-ylmethyl)-N-(prop-2-ynyl)amino]benzoyl-L-γ-glutamyl-D-glutamic acid, N-p-[N-(3,4-dihydro-2,7-dimethyl-4-oxoquinazolin-6-ylmethyl)-N-methylamino]benzoyl-L-γ-glutamyl-D-glutamic acid, N-p-[N-(3,4-dihydro-2,7-dimethyl-4-oxoquinazolin-6-ylmethyl)-N-ethylamino]benzoyl-L-γ-glutamyl-D-glutamic acid, N-p-[N-(3,4-dihydro-2,7-dimethyl-4-oxoquinazolin-6-ylmethyl)-N-(prop-2-ynyl)amino]benzoyl-L-γ-glutamyl-D-glutamic acid, N-p-[N-(3,4-dihydro-2-methoxy-4-oxoquinazolin-6-ylmethyl)-N-methylamino]benzoyl-L-γ-glutamyl-D-glutamic acid, N-p-[N-(3,4-dihydro-2-methoxy-4-oxoquinazolin-6-ylmethyl)-N-ethylamino]benzoyl-L-γ-glutamyl-D-glutamic acid, or N-p-[N-(3,4-dihydro-2-methoxy-4-oxoquinazolin-6-ylmethyl)-N-(prop-2-ynyl)amino]benzoyl-L-γ-glutamyl-D-glutamic acid;

or a pharmaceutically acceptable salt, ester or amide thereof.

9. A compound being:

N-[N-(3,4-dihydro-2-amino-4-oxoquinazolin-6-ylmethyl)-N-methylamino]-o-fluorobenzoyl-L-γ-glutamyl-D-glutamic acid, N-[N-(3,4-dihydro-2-amino-4-oxoquinazolin-6-ylmethyl)-N-ethylamino]-o-fluorobenzoyl-L-γ-glutamyl-D-glutamic acid, N-[N-(3,4-dihydro-2-amino-4-oxoquinazolin-6-ylmethyl)-N-(prop-2-ynyl)amino]-o-fluorobenzoyl-L-γ-glutamyl-D-glutamic acid, N-[N-(3,4-dihydro-2-methyl-4-oxoquinazolin-6-ylmethyl)-N-methylamino]-o-fluorobenzoyl-L-γ-glutamyl-D-glutamic acid, N-[N-(3,4-dihydro-2-methyl-4-oxoquinazolin-6-ylmethyl)-N-ethylamino]-o-fluorobenzoyl-L-γ-glutamyl-D-glutamic acid, N-[N-(3,4-dihydro-2-methyl-4-oxoquinazolin-6-ylmethyl)-N-(prop-2-ynyl)amino]-o-fluorobenzoyl-L-γ-glutamyl-D-glutamic acid, N-[N-(3,4-dihydro-2,7-dimethyl-4-oxoquinazolin-6-ylmethyl)-N-methylamino]-o-fluorobenzoyl-L-γ-glutamyl-D-glutamic acid, N-[N-(3,4-dihydro-2,7-dimethyl-4-oxoquinazolin-6-ylmethyl)-N-ethylamino]-o-fluorobenzoyl-L-γ-glutamyl-D-glutamic acid, N-[N-(3,4-dihydro-2,7-dimethyl-4-oxoquinazolin-6-ylmethyl)-N-(prop-2-ynyl)amino]-o-fluorobenzoyl-L-γ-glutamyl-D-glutamic acid, N-[N-(3,4-dihydro-2-methoxy-4-oxoquinazolin-6-ylmethyl)-N-methylamino]-o-fluorobenzoyl-L-γ-glutamyl-D-glutamic acid, N-[N-(3,4-dihydro-2-methoxy-4-oxoquinazolin-6-ylmethyl)-N-ethylamino]-o-fluorobenzoyl-L-γ-glutamyl-D-glutamic acid, or N-[N-(3,4-dihydro-2-methoxy-4-oxoquinazolin-6-ylmethyl)-N-(prop-2-ynyl)amino]-o-fluorobenzoyl-L-γ-glutamyl-D-glutamic acid;

or a pharmaceutically acceptable salt, ester or amide thereof.

10. A quinazoline according to claim 1, which is free from more than 20% by weight of the corresponding compound in which the first and second amino acid residues of $R^3$ are each in the L-configuration.

11. A pharmaceutical composition comprising a quinazoline according to any of claims 1 to 10 together with a pharmaceutically acceptable diluent or carrier.

12. A quinazoline according to claim 2, wherein the first, N-terminal amino acid residue —NHCH($CO_2$H)—A—CO— has the L-configuration.

13. A quinazoline according to claim 3, wherein the first, N-terminal amino acid residue —NHCH($CO_2$H)—A—CO— has the L-configuration.

14. A quinazoline according to claim 4, wherein $R^3$ is the residue of the dipeptide L-γ-glutamyl-D-aspartic acid.

15. A quinazoline according to claim 4, wherein $R^3$ is the residue of the dipeptide L-γ-glutamyl-D-glutamic acid.

16. A quinazoline according to claim 4, wherein $R^3$ is the residue of the dipeptide L-γ-glutamyl-D-2-aminoadipic acid.

17. A quinazoline according to claim 4, wherein $R^3$ is the residue of the dipeptide L-γ-glutamyl-D-alanine.

18. A method for aiding regression and palliation of a cancer in a warm-blooded animal, said cancer being selected from the group consisting of breast, ovarian and liver cancer and leukaemias, lymphoid malignancies and solid carcinomas and sarcomas, said method comprising the step of administering to the animal a therapeutically effective amount of a quinazoline according to claim 1.

19. A method for aiding regression and palliation of a cancer in a warm-blooded animal, said cancer being selected from the group consisting of breast, ovarian and liver cancer and leukaemias, lymphoid malignancies, said method comprising the step of administering to the animal a therapeutically effective amount of a quinazoline according to claim 1.

* * * * *